United States Patent
Lucks et al.

(10) Patent No.: US 12,325,884 B2
(45) Date of Patent: Jun. 10, 2025

(54) RIBOSWITCH-BASED FLUORIDE SENSING IN CELL-FREE EXTRACT

(71) Applicant: Northwestern University, Evanston, IL (US)

(72) Inventors: Julius B. Lucks, Evanston, IL (US); Walter M. Thavarajah, Chicago, IL (US); Adam D. Silverman, Chicago, IL (US); Michael C. Jewett, Evanston, IL (US)

(73) Assignee: Northwestern University, Evanston, IL (US)

(*) Notice: Subject to any disclaimer, the term of this patent is extended or adjusted under 35 U.S.C. 154(b) by 947 days.

(21) Appl. No.: 17/593,026

(22) PCT Filed: Mar. 3, 2020

(86) PCT No.: PCT/US2020/020800
§ 371 (c)(1),
(2) Date: Sep. 3, 2021

(87) PCT Pub. No.: WO2020/185451
PCT Pub. Date: Sep. 17, 2020

(65) Prior Publication Data
US 2022/0170117 A1 Jun. 2, 2022

Related U.S. Application Data

(60) Provisional application No. 62/813,368, filed on Mar. 4, 2019.

(51) Int. Cl.
*G01N 33/84* (2006.01)
*C12Q 1/6897* (2018.01)
*G01N 33/58* (2006.01)

(52) U.S. Cl.
CPC .......... *C12Q 1/6897* (2013.01); *G01N 33/58* (2013.01); *G01N 33/84* (2013.01); *C12N 2310/16* (2013.01)

(58) Field of Classification Search
CPC .... C12N 15/115; C12Q 1/6897; G01N 33/58; G01N 33/84
See application file for complete search history.

(56) References Cited

U.S. PATENT DOCUMENTS

| 5,478,730 A | 12/1995 | Alakhov et al. |
| 5,556,769 A | 9/1996 | Wu et al. |

(Continued)

FOREIGN PATENT DOCUMENTS

| WO | 2003056914 A1 | 7/2003 |
| WO | 2004013151 A2 | 2/2004 |

(Continued)

OTHER PUBLICATIONS

Espah Borujeni A, Mishler DM, Wang J, Huso W, Salis HM. Automated physics-based design of synthetic riboswitches from diverse RNA aptamers. Nucleic Acids Res. Jan. 8, 2016;44(1):1-13. doi: 10.1093/nar/gkv1289 (cited in IDS Jan. 18, 2023 #14) (Year: 2015).*

(Continued)

*Primary Examiner* — Aaron A Priest
*Assistant Examiner* — Emma R Hoppe
(74) *Attorney, Agent, or Firm* — Quarles & Brady LLP

(57) ABSTRACT

Disclosed are methods and systems for detecting fluoride as a target molecule in a test sample which utilize a cell-protein synthesis (CFPS) reaction and an engineered fluoride-sensing riboswitch. The components used in the disclosed methods and systems may be dried or lyophilized and may be present or immobilized on a paper substrate.

17 Claims, 14 Drawing Sheets

Specification includes a Sequence Listing.

(56) References Cited

U.S. PATENT DOCUMENTS

| | | | |
|---|---|---|---|
| 5,665,563 | A | 9/1997 | Beckler |
| 6,168,931 | B1 | 1/2001 | Swartz et al. |
| 6,518,058 | B1 | 2/2003 | Biryukov et al. |
| 6,783,957 | B1 | 8/2004 | Biryukov et al. |
| 6,869,774 | B2 | 3/2005 | Endo |
| 6,994,986 | B2 | 2/2006 | Swartz et al. |
| 7,118,883 | B2 | 10/2006 | Inoue et al. |
| 7,189,528 | B2 | 3/2007 | Higashide et al. |
| 7,338,789 | B2 | 3/2008 | Swartz et al. |
| 7,387,884 | B2 | 6/2008 | Suzuki et al. |
| 7,399,610 | B2 | 7/2008 | Shikata et al. |
| 8,357,529 | B2 | 1/2013 | Swartz et al. |
| 8,574,880 | B2 | 11/2013 | Bond et al. |
| 8,703,471 | B2 | 4/2014 | Aebi et al. |
| 8,999,668 | B2 | 4/2015 | DeLisa et al. |
| 9,410,170 | B2 | 8/2016 | Calhoun et al. |
| 9,528,130 | B2 | 12/2016 | Datta et al. |
| 9,580,713 | B2 | 2/2017 | Breaker et al. |
| 2004/0209321 | A1 | 10/2004 | Swartz et al. |
| 2005/0170452 | A1 | 8/2005 | Wildt et al. |
| 2006/0211085 | A1 | 9/2006 | Bobrowicz |
| 2006/0234345 | A1 | 10/2006 | Schwartz et al. |
| 2006/0252672 | A1 | 11/2006 | Betenbaugh et al. |
| 2006/0257399 | A1 | 11/2006 | Gerngross et al. |
| 2006/0286637 | A1 | 12/2006 | Hamilton |
| 2007/0026485 | A1 | 2/2007 | DeFrees et al. |
| 2007/0154983 | A1 | 7/2007 | Calhoun et al. |
| 2007/0178551 | A1 | 8/2007 | Gerngross |
| 2008/0138857 | A1 | 6/2008 | Swartz et al. |
| 2014/0295492 | A1 | 10/2014 | Jewett et al. |
| 2016/0060301 | A1 | 3/2016 | Jewett et al. |
| 2016/0312312 | A1 | 10/2016 | Pardee et al. |
| 2016/0362708 | A1 | 12/2016 | Jewett et al. |
| 2018/0016612 | A1 | 1/2018 | Jewett et al. |
| 2018/0016614 | A1 | 1/2018 | Jewett et al. |
| 2018/0265833 | A1* | 9/2018 | Holder .................. C12M 1/34 41/32 |

FOREIGN PATENT DOCUMENTS

| | | |
|---|---|---|
| WO | 2004035605 A2 | 4/2004 |
| WO | 2006102652 A2 | 9/2006 |
| WO | 2006119987 A2 | 11/2006 |
| WO | 2007120932 A2 | 10/2007 |
| WO | 2014144583 A2 | 9/2014 |
| WO | 2017031399 A1 | 2/2017 |
| WO | 2017117539 A1 | 7/2017 |

OTHER PUBLICATIONS

Lu et al. Intrinsic Fluoride Tolerance Regulated by a Transcription Factor. J of Dent Research. 99(11):1270-1278. Jun. 2020 (Year: 2020).*

Baker JL, et al. Widespread genetic switches and toxicity resistance proteins for fluoride. Science. Jan. 13, 2012;335(6065):233-235. Epub Dec. 22, 2011. (Year: 2011).*

Garamella J, et al. The all E. coli TX-TL Toolbox 2.0: A Platform for Cell-Free Synthetic Biology. ACS Synth Biol. Apr. 15, 2016;5(4):344-55. Epub Feb. 9, 2016. (Year: 2016).*

Gregorio, NE, et al.Â A Userâs Guide to Cell-Free Protein Synthesis. Retrieved from https://par.nsf.gov/biblio/10107567.Â Methods and ProtocolsÂ 2.1 Web. Epub Mar. 1, 2019. (Year: 2019).*

IGEM. Part: BBa_B0015 [Internet]. iGEM; Feb. 5, 2019. Available from: https://web.archive.org/web/20190205142531/https://parts.igem.org/Part:BBa_B0015 (Year: 2019).*

IGEM. Part:BBa_B0010 [Internet]. iGEM; Feb. 3, 2019. Available from: https://web.archive.org/web/20190203010039/https://parts.igem.org/wiki/index.php?title=Part:BBa_B0010 (Year: 2019).*

IGEM. Part:BBa_B0012 [Internet]. iGEM; Jan. 12, 2019. Available from: https://web.archive.org/web/20190112050839/https://parts.igem.org/wiki/index.php?title=Part: BBa_B0012 (Year: 2019).*

Espah Borujeni A, et al. Automated physics-based design of synthetic riboswitches from diverse RNA aptamers. Nucleic Acids Res. Jan. 8, 2016;44(1):1-13. Epub Nov. 30, 2015. (Year: 2015).*

Baker JL, et al. Widespread genetic switches and toxicity resistance proteins for fluoride. Science. Jan. 13, 2012;335(6065):233-235. Epub Dec. 22, 2011 (Year: 2012).*

Shin, J. & Noireaux, V. An E. coli cell-free expression toolbox: application to synthetic gene circuits and artificial cells. ACS synthetic biology 1, 29-41, doi:10.1021/sb200016s (2012).

Silverman, A.; Kelley-Loughnane, N.; Lucks, J. B.; Jewett, M. C. Deconstructing Cell-Free Extract Preparation for in Vitro Activation of Transcriptional Genetic Circuitry. ACS Synth. Biol. 2018, 8 (2), 403-414.

Stark, J. C. et al. BioBitsTM Bright: A fluorescent synthetic biology education kit. Sci. Adv. 4, eaat5107 (2018).

Strobel, E. J.; Cheng, L.; Berman, K. E.; Carlson, P. D.; Lucks, J. B. A Ligand-Gated Strand Displacement Mechanism for ZTP Riboswitch Transcription Control. Nat. Chem. Biol. 2019, 15 (11), 1067-1076.

Studier, F. W. & Moffatt, B. A. Use of bacteriophage T7 RNA polymerase to direct selective high-level expression of cloned genes. Journal of molecular biology 189, 113-130 (1986).

Sun, Z.Z., et al., Protocols for Implementing an *Escherichia coli* Based TX-TL Cell-Free Expression System for Synthetic Biology. 2013(79): p. e50762.

Swartz, J. R., Jewett, M. C. & Woodrow, K. A. Cell-free protein synthesis with prokaryotic combined transcription-translation. Methods in molecular biology (Clifton, N.J.) 267, 169-182, doi:10.1385/1-59259-774-2:169 (2004).

Takahashi, M. K. et al. A low-cost paper-based synthetic biology platform for analyzing gut microbiota and host biomarkers. Nat. Commun. 9, 3347 (2018).

Tauriainen, S., Karp, M., Chang, W. & Virta, M. Luminescent bacterial sensor for cadmium and lead. Biosens. Bioelectron. 13, 931-938 (1998).

Travascio, P., Bennet, A. J., Wang, D. Y. & Sen, D. A ribozyme and a catalytic DNA with peroxidase activity: active sites versus cofactor-binding sites. Chem. Biol. 6, 779-787 (1999).

Verosloff, M.; Chappell, J.; Perry, K. L.; Thompson, J. R.; Lucks, J. B. Plant-Dx: A Molecular Diagnostic for Point-of-Use Detection of Plant Pathogens. ACS Synth. Biol. 2019, 8 (4), 902-905.

Watters, K. E., Strobel, E. J., Angela, M. Y., Lis, J. T. & Lucks, J. B. Cotranscriptional folding of a riboswitch at nucleotide resolution. Nat. Struct. Mol. Biol. 23, 1124 (2016).

Wen, K.Y., et al., A Cell-Free Biosensor for Detecting Quorum Sensing Molecules in P. aeruginosa-Infected Respiratory Samples. ACS Synthetic Biology, 2017. 6(12): p. 2293-2301.

Wickiser, J. K.; Winkler, W. C.; Breaker, R. R.; Crothers, D. M. The Speed of RNA Transcription and Metabolite Binding Kinetics Operate an FMN Riboswitch. Mol. Cell 2005, 18 (1), 49-60.

Wu, M. J.; Andreasson, J. O. L.; Kladwang, W.; Greenleaf, W. J.; Das, R. Automated Design of Diverse Stand-Alone Riboswitches. ACS Synth. Biol. 2019, 8 (8), 1838-1846.

Yang, W. C. et al. Cell-free production of transducible transcription factors for nuclear reprogramming. Biotechnology and bioengineering 104, 1047-1058, doi:10.1002/bit.22517 (2009).

Zadeh, J. N. et al. Nupack: analysis and design of nucleic acid systems. J. Comput. Chem. 32, 170-173 (2011).

Zawada, J. F. et al. Microscale to manufacturing scale-up of cell-free cytokine production—a new approach for shortening protein production development timelines. Biotechnology and bioengineering 108, 1570-1578, doi:10.1002/bit.23103 (2011).

Zhao, B.; Guffy, S. L.; Williams, B.; Zhang, Q. An Excited State Underlies Gene Regulation of a Transcriptional Riboswitch. Nat. Chem. Biol. 2017, 13 (9), 968-974.

Zhou, Y.; Zhang, J. F.; Yoon, J. Fluorescence and Colorimetric Chemosensors for Fluoride-Ion Detection. Chem. Rev. 2014, 114 (10), 5511-5571.

Alam, K. K., Tawiah, K. D., Lichte, M. F., Porciani, D. & Burke, D. H. A Fluorescent Split Aptamer for Visualizing RNA—RNA Assembly in Vivo. ACS Synth. Biol. 6, 1710-1721 (2017).

Alam, K. K.; Jung, J. K.; Verosloff, M. S.; Clauer, P. R.; Lee, J. W.; Capdevila, D. A.; Pastén, P. A.; Giedroc, D. P.; Collins, J. J.; Lucks,

(56) References Cited

OTHER PUBLICATIONS

J. B. Rapid, Low-Cost Detection of Water Contaminants Using Regulated in Vitro Transcription. bioRxiv 2019. https://doi.org/10.1101/619296.

Baker, J. L. et al. Widespread genetic switches and toxicity resistance proteins for fluoride. Science (80). 335, 233-235 (2012).

Berens, C. & Suess, B. Riboswitch engineering—making the all-important second and third steps. Curr. Opin. Biotechnol. 31, 10-15 (2015).

Boussebayle, A.; Torka, D.; Ollivaud, S.; Braun, J.; Bofill-Bosch, C.; Dombrowski, M.; Groher, F.; Hamacher, K.; Suess, B. Next-Level Riboswitch Development—Implementation of Capture-Selex Facilitates Identification of a New Synthetic Riboswitch. Nucleic Acids Res. 2019, 47 (9), 4883-4895.

Calhoun, K. A. & Swartz, J. R. in (ed. Grandi, G.) 3-17 (Humana Press, 2007). doi:10.1007/978-1-59745-388-2_1.

Carlson, E. D., Gan, R., Hodgman, C. E. & Jewett, M. C. Cell-free protein synthesis: applications come of age. Biotechnol. Adv. 30, 1185-1194 (2012).

Caschera, F. & Noireaux, V. Synthesis of 2.3 mg/ml of protein with an all Escherichia coli cell-free transcription-translation system. Biochimie 99, 162-168, doi:10.1016/j.biochi.2013.11.025 (2014).

Chappell, J., Jensen, K. & Freemont, P. S. Validation of an entirely in vitro approach for rapid prototyping of DNA regulatory elements for synthetic biology. Nucleic acids research 41, 3471-3481, doi:10.1093/nar/gkt052 (2013).

Chappell, J., Westbrook, A., Verosloff, M. & Lucks, J. B. Computational design of small transcription activating RNAs for versatile and dynamic gene regulation. Nat. Commun. 8, 1051 (2017).

Doull, J.; Boekelheide, K.; Farishian, B. G.; Isaacson, R. L.; Klotz, J. B.; Kumar, J. V; Limeback, H.; Poole, C.; Puzas, J. E.; Reed, N. M. R. Fluoride in Drinking Water: A Scientific Review of EPA's Standards. Natl. Acad. Washingt. 2006, 205-223.

Drogalis, L. K.; Batey, R. T. Requirements for Efficient Cotranscriptional Regulatory Switching in Designed Variants of the Bacillus Subtilis PbuE Adenine-Responsive Riboswitch. bioRxiv 2018. https://doi.org/10.1101/372573.

Edition, F. Guidelines for drinking water quality. WHO Chron. 38, 104-108 (2011)./ World Health Organization. Guidelines for Drinking-Water Quality. WHO Chron. 2011, 38 (4), 104-108.

Espah Borujeni, A.; Mishler, D. M.; Wang, J.; Huso, W.; Salis, H. M. Automated Physics-Based Design of Synthetic Riboswitches from Diverse RNA Aptamers. Nucleic Acids Res. 2015, 44 (1), 1-13.

Etzel, M. & Morl, M. Synthetic Riboswitches: From Plug and Pray toward Plug and Play. Biochemistry 56, 1181-1198 (2017).

F, R., G, F., E, M., Martinez Cruz, M. & Bergen M.J., van. Fluorosis dental en la población infantil en las cercanías del volcán Irazú, Costa Rica. (2014)./ Rojas Zuniga, F.; Floor, G.; Malavassi, E.; Martinez Cruz, M.; Van Bergen, M. Fluorosis Dental En La Población Infantil En Las Cercanías Del Volcán Irazú, Costa Rica. Congr. Latinoam. Estud. Química Paraguay 2014.

Frieda, K. L.; Block, S. M. Direct Observation of Cotranscriptional Folding in an Adenine Riboswitch. Science (80-. ). 2012, 338 (6105), 397-400.

Garcia-González, V., et al., Regulation of the Pseudomonas sp. Strain ADP Cyanuric Acid Degradation Operon. Journal of Bacteriology, 2005. 187(1): p. 155-167.

Gräwe, A.; Dreyer, A.; Vornholt, T.; Barteczko, U.; Buchholz, L.; Drews, G.; Ho, U. L.; Jackowski, M. E.; Kracht, M.; Lüders, J. A Paper-Based, Cell-Free Biosensor System for the Detection of Heavy Metals and Date Rape Drugs. PLoS One 2019, 14 (3), e0210940.

Greenlee, E. B.; Stav, S.; Atilho, R. M.; Brewer, K. I.; Harris, K. A.; Malkowski, S. N.; Mirihana Arachchilage, G.; Perkins, K. R.; Sherlock, M. E.; Breaker, R. R. Challenges of Ligand Identification for the Second Wave of Orphan Riboswitch Candidates. RNA Biol. 2018, 15 (3), 377-390.

Gupta, S.; Sarkar, S.; Katranidis, A.; Bhattacharya, J. Development of a Cell-Free Optical Biosensor for Detection of a Broad Range of Mercury Contaminants in Water: A Plasmid DNA-Based Approach. ACS Omega 2019, 4 (5), 9480-9487.

Haklay, M. & Weber, P. Openstreetmap: User-generated street maps. Ieee Pervas Comput 7, 12-18 (2008).

Hodgman, C. E. & Jewett, M. C. Cell-free synthetic biology: thinking outside the cell. Metab. Eng. 14, 261-269 (2012).

Hong, S. H. et al. Improving Cell-Free Protein Synthesis through Genome Engineering of Escherichia coli Lacking Release Factor 1. Chembiochem : a European journal of chemical biology, doi:10.1002/cbic.201402708 (2015).

Hu, C. Y., Varner, J. D. & Lucks, J. B. Generating Effective Models and Parameters for RNA Genetic Circuits. ACS Synth. Biol. 4, 914-926 (2015).

Hua, A., et al., Development of a bacterial bioassay for atrazine and cyanuric acid detection. Frontiers in Microbiology, 2015. 6: p. 211.

Huang, A. et al. BioBitsTM Explorer: A modular synthetic biology education kit. Sci. Adv. 4, eaat5105 (2018).

Jewett, M. C. & Swartz, J. R. Mimicking the Escherichia coli cytoplasmic environment activates long-lived and efficient cell-free protein synthesis. Biotechnology and bioengineering 86, 19-26, doi:10.1002/bit.20026 (2004).

Jia, K., et al., A lower limit of detection for atrazine was obtained using bioluminescent reporter bacteria via a lower Incubation temperature. Ecotoxicology and Environmental Safety, 2012. 84: p. 221-226.

Karim, A. S. & Jewett, M. C. A cell-free framework for rapid biosynthetic pathway prototyping and enzyme discovery. Metabolic engineering 36, 116-126, doi:10.1016/j.ymben.2016.03.002 (2016).

Karzbrun, E.; Shin, J.; Bar-Ziv, R. H.; Noireaux, V. Coarse-Grained Dynamics of Protein Synthesis in a Cell-Free System. Phys. Rev. Lett. 2011, 106 (4), 48104.

Kelley, S. O. et al. Advancing the speed, sensitivity and accuracy of biomolecular detection using multi-length-scale engineering. Nat. Nanotechnol. 9, 969 (2014).

Krishnamachari, K. A. Skeletal fluorosis in humans: a review of recent progress in the understanding of the disease. Prog. Food Nutr. Sci. 10, 279-314 (1986).

Kwon, Y. C. & Jewett, M. C. High-throughput preparation methods of crude extract for robust cell-free protein synthesis. Scientific reports 5, 8663, doi:10.1038/srep08663 (2015).

Maheshwari, R. C. Fluoride in drinking water and its removal. J. Hazard. Mater. 137, 456-463 (2006).

Mandal, M. & Breaker, R. R. Gene regulation by riboswitches. Nat. Rev. Mol. cell Biol. 5, 451 (2004).

Mascarenhas, A. K. Risk factors for dental fluorosis: a review of the recent literature. Pediatr. Dent. 22, 269-277 (2000).

McCown, P. J., Corbino, K. A., Stav, S., Sherlock, M. E. & Breaker, R. R. Riboswitch diversity and distribution. Rna 23, 995-1011 (2017).

McNerney, M. P.; Zhang, Y.; Steppe, P.; Silverman, A. D.; Jewett, M. C.; Styczynski, M. P. Point-of-Care Biomarker Quantification Enabled by Sample-Specific Calibration. Sci. Adv. 2019, 5 (9), eaax4473.

Moore, S. J.; MacDonald, J. T.; Wienecke, S.; Ishwarbhai, A.; Tsipa, A.; Aw, R.; Kylilis, N.; Bell, D. J.; McClymont, D. W.; Jensen, K.; et al. Rapid Acquisition and Model-Based Analysis of Cell-Free Transcription—Translation Reactions from Nonmodel Bacteria. Proc. Natl. Acad. Sci. 2018, 115 (19).

Muranaka, Norihito, et al. "Efficient design strategy for whole-cell and cell-free biosensors based on engineered riboswitches." Analytical Letters 42.1 (2009): 108-122.

Ogawa, A. Rational design of artificial riboswitches based on ligand-dependent modulation of internal ribosome entry in wheat germ extract and their applications as label-free biosensors. RNA (2011).

Onda, K., LoBuglio, J. & Bartram, J. Global access to safe water: accounting for water quality and the resulting impact on MDG progress. Int. J. Environ. Res. Public Health 9, 880-894 (2012).

Organization, W. H. World health statistics 2016: monitoring health for the SDGs sustainable development goals. (World Health Organization, 2016).

Pardee, K. et al. Paper-Based Synthetic Gene Networks. Cell 159, 940-954 (2014).

(56) References Cited

OTHER PUBLICATIONS

Pardee, K. et al. Rapid, low-cost detection of Zika virus using programmable biomolecular components. Cell 165, 1255-1266 (2016).

Ren, A., Rajashankar, K. R. & Patel, D. J. Fluoride ion encapsulation by Mg 2+ ions and phosphates in a fluoride riboswitch. Nature 486, 85 (2012).

Salehi, A. S. M. et al. Cell-free protein synthesis approach to biosensing hTRβ-specific endocrine disruptors. Anal. Chem. 89, 3395-3401 (2017).

Schmidt, C. M. & Smolke, C. D. RNA Switches for Synthetic Biology. Cold Spring Harb. Perspect. Biol. 11, (2019).

Selifonova, O., Burlage, R. & Barkay, T. Bioluminescent sensors for detection of bioavailable Hg (II) in the environment. Appl. Environ. Microbiol. 59, 3083-3090 (1993).

\* cited by examiner

Figure 13

| | |
|---|---|
| pJBL3752 (SEQ ID NO: 1): Anderson Promoter BBa_J23119_SpeI / B.CEREUS FLUORIDE RIBOSWITCH / ribosome binding sequence / Superfolder GFP coding sequence / T1/TE terminator | ttgacagctagctcagtcctaggtataatactagtttaTAGGCGATGGAGTTCGCCATAAACGCTGCTTAGCTAATGACTCCTACCAGTATCACTACTG GTAGGAGTCTCTATTTTTTaggaggaaggatctatgagcaaaggagaagaacttttcactggagtgtcccaattctgttgaattagatgtgatgttaatggcacaaattctgtcc gtgagagggtgaaggtgatgctacaaacgtaaaactcaccctaaatttattgcactctgaaacctacctgttccgtggccaaacctacctgttccgtgacctatgttcaatgttttcc gtatccggatcacatgaaacggcatgactttttcaagagtgccatgcccgaaggttacgtcaggagtacaagagtaaacaagatgacgggaccctacaagacgctgctgaagtcaagtt gaaggtgataccctgttaatgtatcgtatcgagttaagggatatattgatttttaaagatggcagacaagatgagccctccgtgccatcaagttaatggacgtgatactatacaccacgctatatagacaa caaagaatgaatcaaattcaaactcgtcctttcgaaaattcaaactccacagaagcgttgaaggatgtttccgttcaactagccagaccattatcaacctagaacgcgttttaactcaaattcaacatcaaatataccacaatgcgcatgccctgtcctttaccagacaa ccattacctgcaacaatcgtgcctttcgaaaggatccaacaaaagcgtgaccacactgctcttaccacacgcgcttgagttttgaactgccgctggatttaccacatgcatgctttaaaccttaaccagga tccaaactcgagtgaaggatctccaggcatcaaataaaacgaaaggctcagtcgaaagactggggcttttcttgttgtcgtgacgctctctactagagtcacactgcc tcaccttcgggtgggcctttctgcgttata |
| pJBL7025 (SEQ ID NO: 2): Anderson Promoter BBa_J23119_SpeI / B.CEREUS FLUORIDE RIBOSWITCH / ribosome binding sequence / Catechol 2, 3-dioxygenase coding sequence / T1/TE terminator | ttgacagctagctcagtcctaggtataatactagtttaTAGGCGATGGAGTTCGCCATAAACGCTGCTTAGCTAATGACTCCTACCAGTATCACTACTG GTAGGAGTCTCTATTTTTTaggaggaaggatctatgaacaaaggtgtaatgcgaccatgtgaccggccaagtcagctgcgttgaacatgaacatgagcaactacgtcgag ttgctggcctgatcgagatgaccgtgaccgggccggccgtgaccgcgaaggtgctatcgaaggcttccgctgctacgcgaggctgaccagtggatataacagttttatggg tttcaaggttgtgatgaggatgctctccggcaactgaagctgagcggatcatgaccgtgtgccgttgagcagctaccccggagttgtgccggcggcgtgcgttccaggt ccccctccggcatccactcctgagttgtatgcagaccaaggaatatactggaagttgggatttggaatgacgtcaatcagcgagcatgccgccgcgcatcaatggtggcatccgcgctcagtct gtcgaccaaggccacgacgtgccgaattgccgcgaccatgccggccatgccgttcaccaagtgctgcgttcatctgcgccgaacaaggtgctcgccgcgacctgatctcatgaccg cacaaaccgtgacctgaccacccgaccacgtcggccaagcgatcttttaccacgcgaatcttaacggcgaaccgatcagtgcgaccgtgaccagtgacctgcgtgaccctgaacactcgagttaaggatc tccaggcatcaaataaaacgaaaggctcagtcagtcgaaagactggggcttttgttgttgttcacactggctcaccttctactagagtcacactggctcaccttcgggtgggcctt tctgcgttata |
| pJBL7026 (SEQ ID NO: 3): Anderson Promoter BBa_J23119_SpeI / B.CEREUS FLUORIDE RIBOSWITCH / 3-Way Junction Dimeric Broccoli coding sequence / T1/TE terminator | ttgacagctagctcagtcctaggtataatactagtttaTAGGCGATGGAGTTCGCCATAAACGCTGCTTAGCTAATGACTCCTACCAGTATCACTACTG GTAGGAGTCTCTATTTTTTcccacatactctgatgatccgagacggtggggtccagatattcgtatcgtcgagtagagtgtggctcggatcattcatgcaagagacggtcggtcc agatattcgtatcgtcgagtagagtgtggctcttgccatgtgtatgtgggccaggcatcaaataaaacgaaaggctcagtcagtcgaaagactgggcctttcgttttatcgttgttgttcggtga acgtctctactagagtcacactggctcaccttcgggtgggccttttctgcgttata |

Figure 14

| Site | GPS Coordinates | Source | Measured [F⁻] (ppm) | Activation | Negative Control | Positive Control |
|------|-----------------|--------|---------------------|------------|------------------|------------------|
| A | 9°58'30"N 84°00'20"W | Indoor Faucet | 0.2 | No | Off | On |
| B | 10°00'00"N 83°57'30"W | Muddy Ditch | 0.3 | No | Off | On |
| C | 10°00'40"N 83°57'10"W | Indoor Faucet | 0.2 | No | Off | On |
| D | 9°56'50"N 83°51'50"W | Outdoor Supply | 1 | Yes | Off | On |
| E | 9°58'10"N 83°49'40"W | Muddy Ditch | 1.2 | Yes | Off | On |
| F | 10°00'10"N 83°46'50"W | Outdoor Supply | 0.5 | No | Off | On |
| G | 9°56'30"N 83°46'40"W | River | 0.1 | No | Off | On |
| H | 9°57'10"N 83°46'20"W | River | 0.3 | No | Off | On |
| I | 9°57'20"N 83°46'20"W | River | 0.3 | No | Off | On |

SEQUENCE LISTING

<160> NUMBER OF SEQ ID NOS: 3

<210> SEQ ID NO 1
<211> LENGTH: 1001
<212> TYPE: DNA

<213> ORGANISM: Artificial
<220> FEATURE:
<223> OTHER INFORMATION: Expression Cassette for Expressing Superfolder
      GFP Using Fluoride Riboswitch

<400> SEQUENCE: 1

```
ttgacagcta gctcagtcct aggtataata ctagtttata ggcgatggag ttcgccataa    60
acgctgctta gctaatgact cctaccagta tcactactgg taggagtcta ttttttttagg   120 aggaaggatc tatgagcaaa ggagaagaac ttttcactgg agttgtccca attcttgttg    180
aattagatgg tgatgttaat gggcacaaat tttctgtccg tggagagggt gaaggtgatg    240
ctacaaacgg aaaactcacc cttaaattta tttgcactac tggaaaacta cctgttccgt    300
ggccaacact tgtcactact ctgacctatg gtgttcaatg cttttcccgt tatccggatc    360
acatgaaacg gcatgacttt ttcaagagtg ccatgcccga aggttatgta caggaacgca    420
ctatatcttt caaagatgac gggacctaca agacgcgtgc tgaagtcaag tttgaaggtg    480 ataccttgt taatcgtatc gagttaaagg gtattgattt aaagaagat ggaaacattc    540 ttggacacaa actcgagtac aactttaact cacacaatgt atacatcacg gcagacaaac    600
aaaagaatgg aatcaaagct aacttcaaaa ttcgccacaa cgttgaagat ggttccgttc    660
aactagcaga ccattatcaa caaaatactc caattggcga tggccctgtc cttttaccag    720
acaaccatta cctgtcgaca caatctgtcc tttcgaaaga tcccaacgaa aagcgtgacc    780
acatggtcct tcttgagttt gtaactgctg ctgggattac acatggcatg gatgagctct    840
acaaataagg atccaaactc gagtaaggat ctccaggcat caaataaaac gaaaggctca    900
gtcgaaagac tgggcctttc gttttatctg ttgtttgtcg gtgaacgctc tctactagag    960
tcacactggc tcaccttcgg gtgggccttt ctgcgtttat a                       1001
```

<210> SEQ ID NO 2
<211> LENGTH: 1211
<212> TYPE: DNA
<213> ORGANISM: Artificial
<220> FEATURE:
<223> OTHER INFORMATION: Expression Cassette for Expressing Catechol
      2,3-dehydrogenase Using Fluoride Riboswitch

<400> SEQUENCE: 2

```
ttgacagcta gctcagtcct aggtataata ctagtttata ggcgatggag ttcgccataa    60
acgctgctta gctaatgact cctaccagta tcactactgg taggagtcta ttttttttagg   120 aggaaggatc tatgaacaaa ggtgtaatgc gaccgggcca tgtgcagctg cgtgtactgg    180
acatgagcaa ggccctggaa cactacgtcg agttgctggg cctgatcgag atggaccgtg    240
acgaccaggg ccgtgtctat ctgaaggctt ggaccgaagt ggataagttt tccctggtgc    300
tacgcgaggc tgacgagccg ggcatggatt ttatgggttt caaggttgtg gatgaggatg    360
ctctccggca actggagcgg gatctgatgg catatggctg tgccgttgag cagctacccg    420
caggtgaact gaacagttgt ggccggcgcg tgcgcttcca ggcccctcc gggcatcact    480 tcgagttgta tgcagacaag gaatatactg gaaagtgggg tttgaatgac gtcaatcccg    540
aggcatggcc gcgcgatctg aaaggtatgg cggctgtgcg tttcgaccac gccctcatgt    600
atggcgacga attgccggcg acctatgacc tgttcaccaa ggtgctcggt ttctatctgg    660
ccgaacaggt gctggacgaa aatggcacgc gcgtcgccca gtttctcagt ctgtcgacca    720
aggcccacga cgtggccttc attcaccatc cggaaaaagg ccgcctccat catgtgtcct    780
tccacctcga aacctgggaa gacttgcttc gcgccgccga cctgatctcc atgaccgaca    840
```

```
catctatcga tatcggccca acccgccacg gcctcactca cggcaagacc atctacttct        900
tcgacccgtc cggtaaccgc aacgaagtgt tctgcggggg agattacaac tacccggacc        960
acaaaccggt gacctggacc accgaccagc tgggcaaggc gatcttttac cacgaccgca       1020
ttctcaacga acgattcatg accgtgctga cctgataagg atccaaactc gagtaaggat       1080
ctccaggcat caaataaaac gaaaggctca gtcgaaagac tgggcctttc gttttatctg       1140
ttgtttgtcg gtgaacgctc tctactagag tcacactggc tcaccttcgg gtgggccttt       1200
ctgcgtttat a                                                            1211

<210> SEQ ID NO 3
<211> LENGTH: 398
<212> TYPE: DNA
<213> ORGANISM: Artificial
<220> FEATURE:
<223> OTHER INFORMATION: Expression Cassette for Expressing 3-way
      Junction Dimeric Broccoli Coding Sequence Using Fluoride
      Riboswitch

<400> SEQUENCE: 3
ttgacagcta gctcagtcct aggtataata ctagtttata ggcgatggag ttcgccataa         60
acgctgctta gctaatgact cctaccagta tcactactgg taggagtcta ttttttttccc      120 acatactctg atgatccgag acggtcgggt ccagatattc gtatctgtcg agtagagtgt       180
gggctcggat cattcatggc aagagacggt cgggtccaga tattcgtatc tgtcgagtag       240
agtgtgggct cttgccatgt gtatgtgggc caggcatcaa ataaaacgaa aggctcagtc       300
gaaagactgg gcctttcgtt ttatctgttg tttgtcggtg aacgctctct actagagtca       360
cactggctca ccttcgggtg ggcctttctg cgtttata                               398
```

RIBOSWITCH-BASED FLUORIDE SENSING IN CELL-FREE EXTRACT

CROSS-REFERENCE TO RELATED PATENT APPLICATIONS

This application is the U.S. National Stage of PCT/US2020/020800 having international filing date of Mar. 3, 2020, which claims the benefit of priority under 35 U.S.C. § 119(e) to U.S. Provisional Application No. 62/813,368, filed on Mar. 4, 2019. The content of each of the above applications is incorporated herein by reference in its entirety.

STATEMENT REGARDING FEDERALLY SPONSORED RESEARCH OR DEVELOPMENT

This invention was made with government support under grant 1650040 awarded by the National Science Foundation and under grant FA8650-15-2-5518 awarded by the Air Force Research Laboratory. The government has certain rights in the invention.

SEQUENCE LISTING

This application contains, as a separate part of the disclosure, a Sequence Listing in computer readable form (filename: 702581.01704_SeqList.txt; Created: Feb. 24, 2020; 4,441 bytes), which is incorporated by reference in its entirety.

BACKGROUND

The field of the invention relates to cell-free protein synthesis (CFPS) systems. In particular, the field of the invention relates to the use of CFPS systems for in vitro detection of target molecules using cellular extracts.

Cell-free protein synthesis (CFPS) using extracts from prokaryotic source strains such as *E. coli* has undergone a transformational shift from an exploratory platform used in the discovery of the genetic code to a present-day, high-yielding protein production platform.[37] This shift is fueled by the open nature of this system, allowing for rapid combination, supplementation, and optimization of the physiochemical environment for increasing protein yields and batch reaction duration.[28,39] Now, cell-free systems are seen as a complement to in vivo protein expression and can be used as both a prototyping platform due to their simplicity, easiness, and modular design for protein expression[40-42] as well as a large-scale production platform for difficult to express proteins in vivo.[43]

Here, we disclose a platform that utilizes CFPS for in vitro sensing of fluoride. The components of the platform are modular and can be preserved for long-term use.

SUMMARY

Disclosed are methods, systems, and components thereof for detecting fluoride as a target molecule in a test sample. The disclosed methods and systems utilize a cell-protein synthesis (CFPS) reaction and an engineered fluoride-sensing riboswitch. The components used in the disclosed methods and systems may be dried or lyophilized and may be present or immobilized on a paper substrate.

The disclosed methods may be performed to detect fluoride as a target molecule in a biological or environmental sample and may include step of: (i) obtaining a biological or environmental sample which may or may not contain fluoride; and (ii) adding the sample to a cell-free protein synthesis (CFPS) reaction, where if the fluoride is present in the sample then an detectable output is generated indicating that fluoride is present in the sample.

Also disclosed are devices, kits, and components thereof which may be utilized in the disclosed methods for detecting fluoride in a biological or environmental sample. Optionally, the components of the disclosed devices and kits may be preserved, for example, by freeze-drying or lyophilization, and may be present on a substrate, such as a paper substrate used as a paper test article.

before image capture at 60 minutes. The arrow indicates a tube in which yellow color clearly discernable. (c) Time lapse of rehydrated lyophilized reactions incubated at 37° C. in the absence (top) and presence (bottom) of 1 mM NaF. The arrows indicate time points in which yellow color is clearly discernable.

Figure 4:
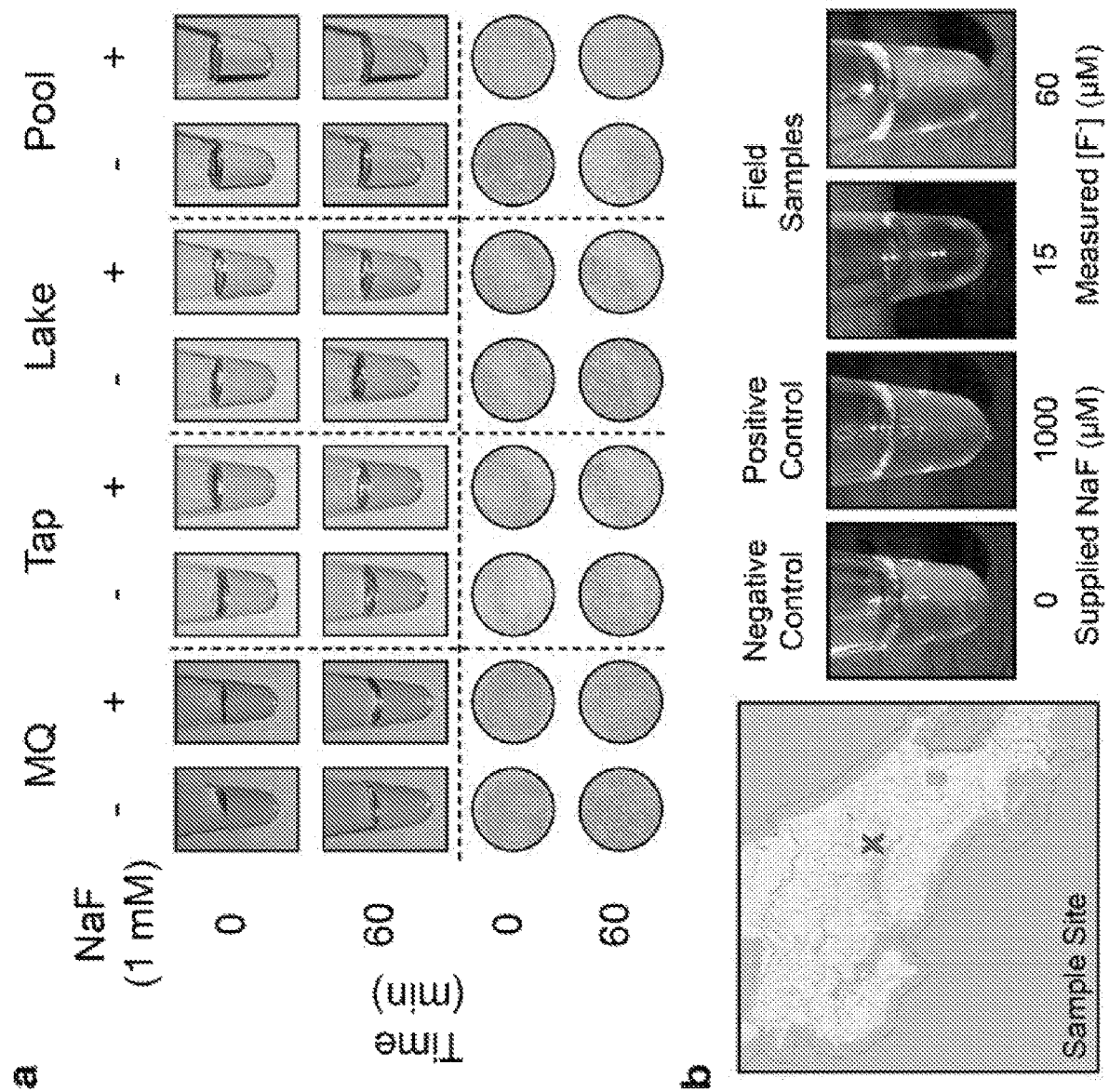

FIG. 4. The cell-free fluoride riboswitch biosensor functions with real-world water samples and is not impacted by long-term storage and distribution. (a) Cell-free reactions rehydrated with various water samples with or without 1 mM NaF added. Lyophilized reactions in tubes are shown above lyophilized reactions on chromatography paper before and after one-hour incubation at 37° C. MQ=laboratory grade Milli-Q water; Tap=tap water; Lake=unfiltered Lake Michigan water; Pool=unfiltered outdoor pool water. Uncropped photos of chromatography paper experiments are available in FIG. 12. Yellow color is clearly discernable in each (+) sample tube at the 60 minute time point. A color change is clearly discernable in (+) sample chromatography paper at the 60 minute time point. (b) Field testing of lyophilized cell-free reactions rehydrated with water sampled in Cartago, Costa Rica. Geographical map from OpenStreetMap22. The positive control contained 1 mM NaF in the reaction before lyophilization. The negative control was rehydrated with Milli-Q water, and the positive control and each test were rehydrated with 20 μL of unprocessed field sample followed by body-heat incubation for five hours. Measured fluoride concentrations obtained using a fluoride sensing electrode. Field samples are from sites B and E in FIG. 14. Yellow color is clearly visible in the Positive Control and in the 60 μM Field Sample.

Figure 5:
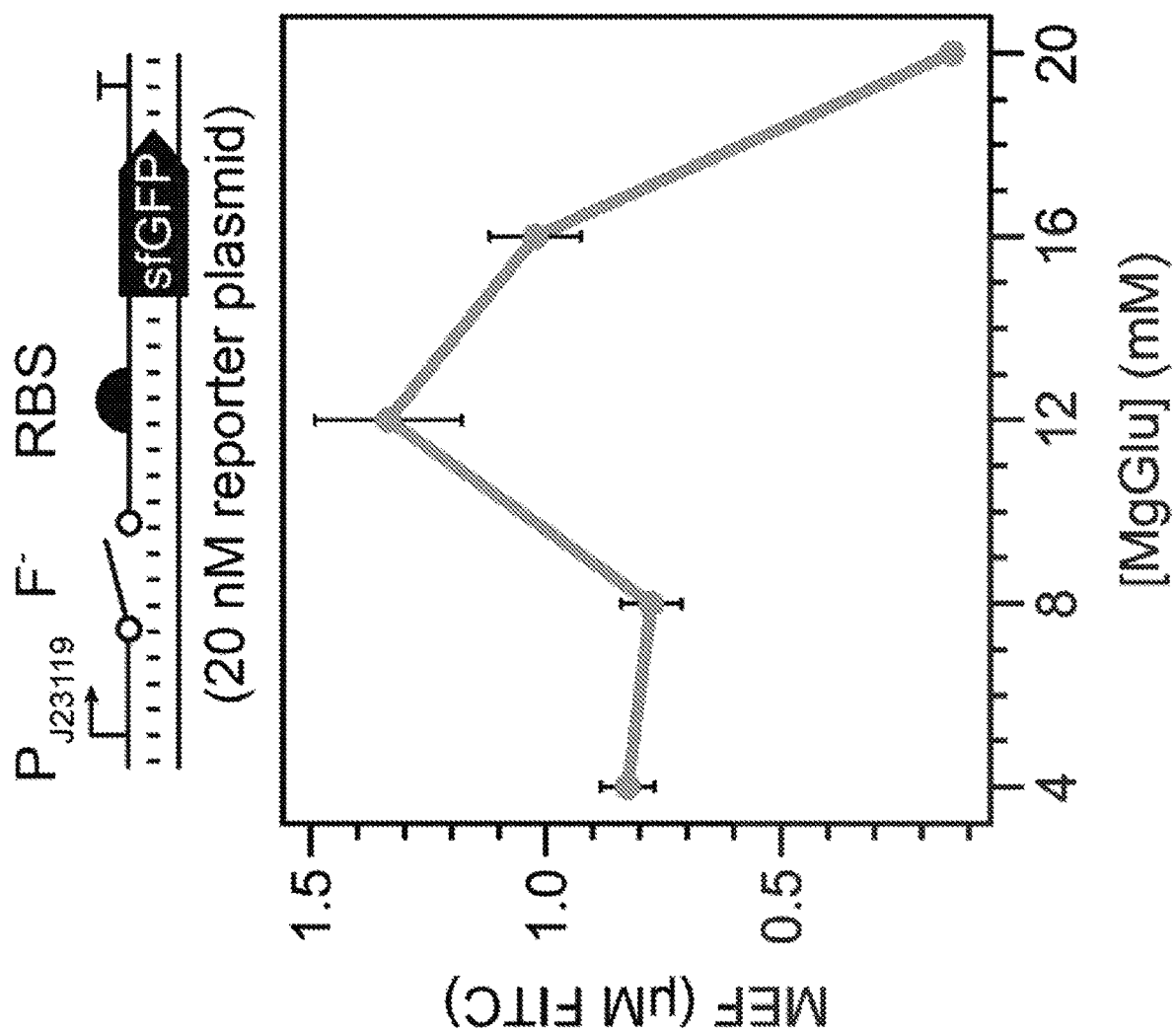

FIG. 5. Fluoride riboswitch magnesium optimization. Reactions were supplied with 1 mM NaF and varying magnesium glutamate as indicated. Data shown are endpoint measurements from an eight-hour experiment. Error bars represent one standard deviation from three technical replicates. This experiment indicated that a magnesium glutamate concentration of 12 mM gave optimal fluorescence, though we note that optimal magnesium concentration can vary between extracts.

Figure 6:
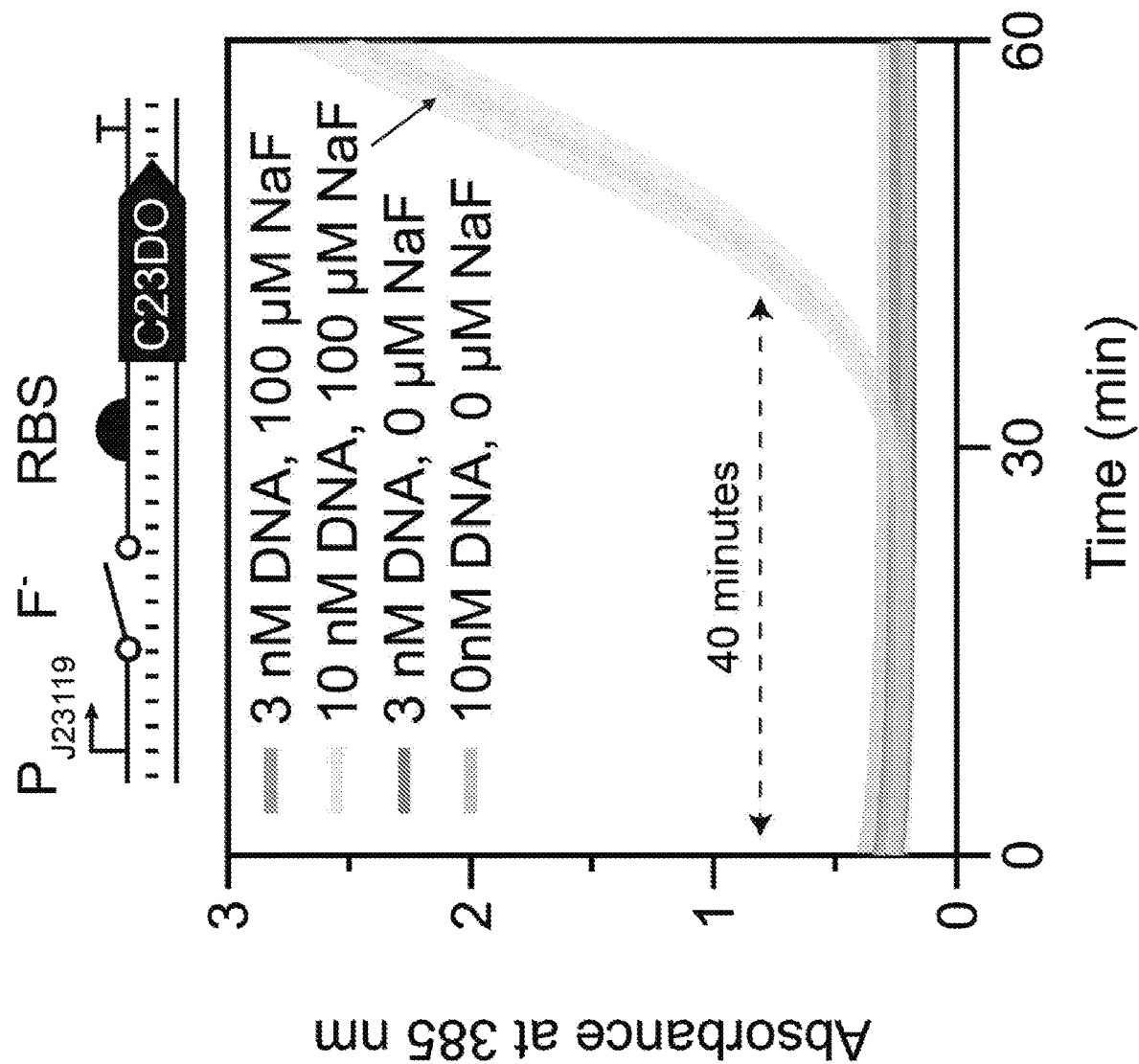

FIG. 6. Kinetic traces for reaction conditions depicted in FIG. 3B. This experiment was run at 37° C. to best mirror experimental conditions for reactions run in PCR tubes. Visible activation is seen in 40 minutes for the condition with 10 nM biosensor DNA and 100 μM NaF (marked with an arrow), corroborating the results depicted in FIG. 3B. Trajectories represent average and error shading represents one standard deviation from three technical replicates.

Figure 7:
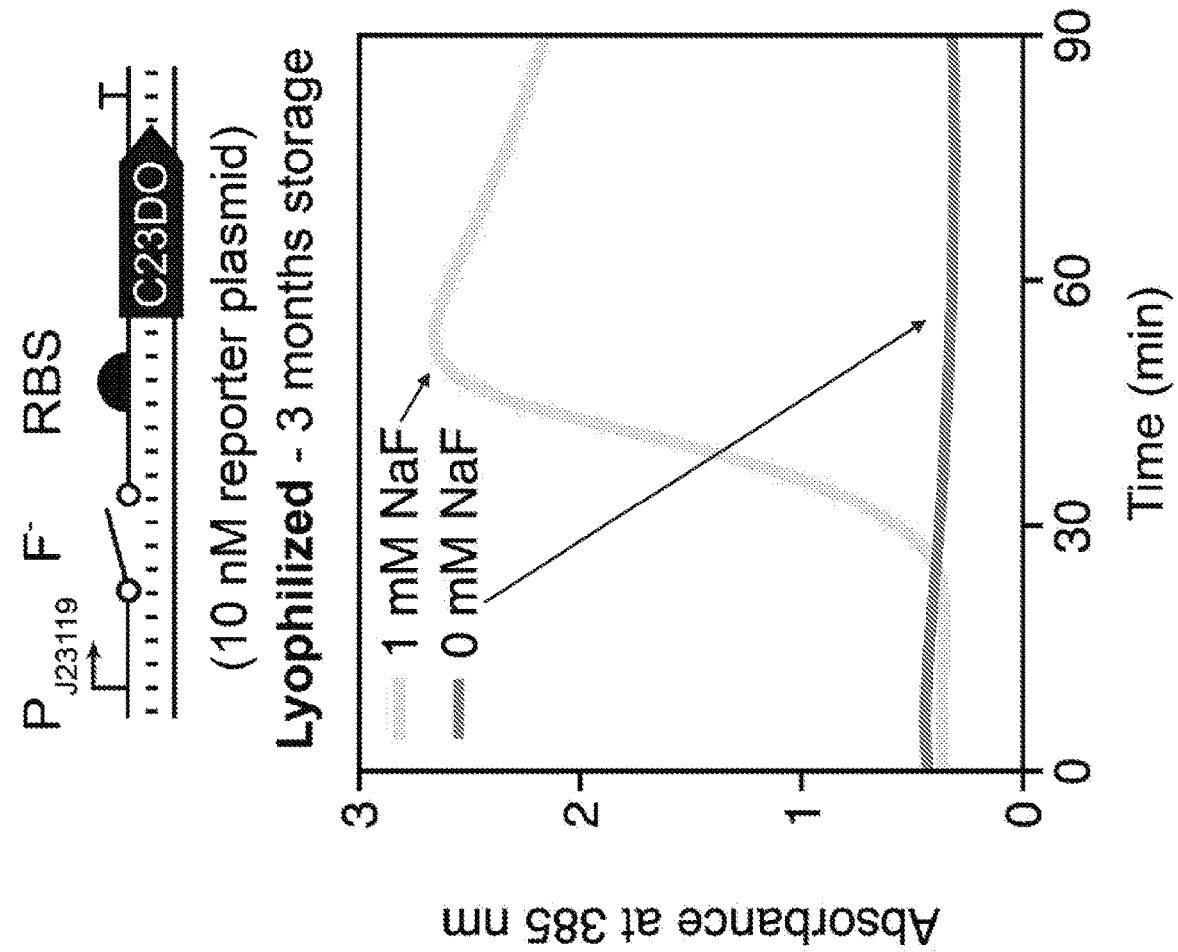

FIG. 7. Lyophilized reactions remain viable after three months of storage in desiccant. Reactions were stored in darkness under ambient conditions before rehydration with 20 μL of water with or without 1 mM NaF. Trajectories, marked by arrows, represent data from one experiment.

Figure 8:
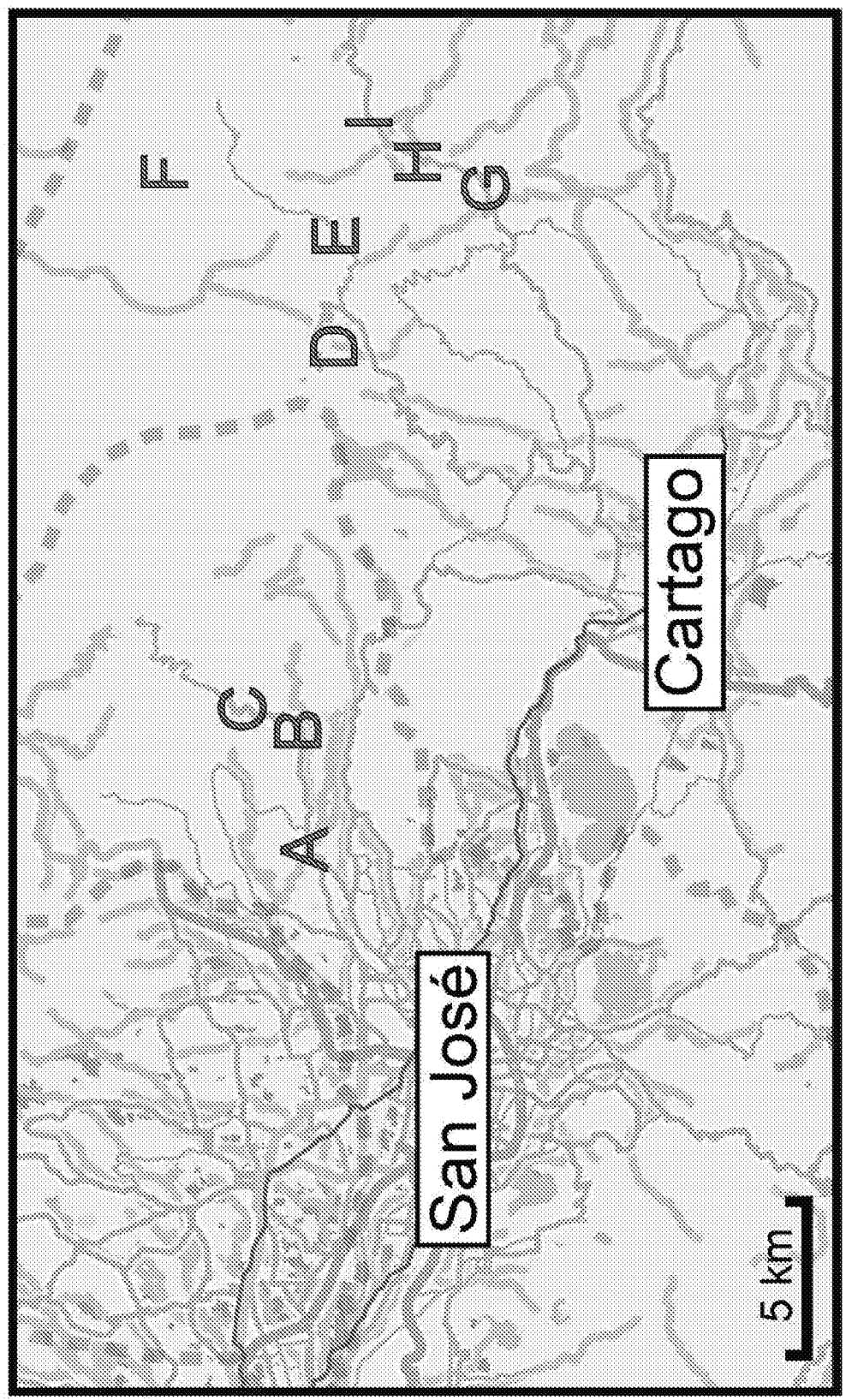

FIG. 8. Map of Costa Rican water sampling locations. Sampling locations were determined from a previously published report about the presence of fluoride in water within this region[1]. Each letter represents a unique source where 50 ml of water was sampled. Locations center around the Irazu volcano, a known source of fluoridated salts[1]. Data presented in FIG. 4B is from locations B and E.

Figure 9:
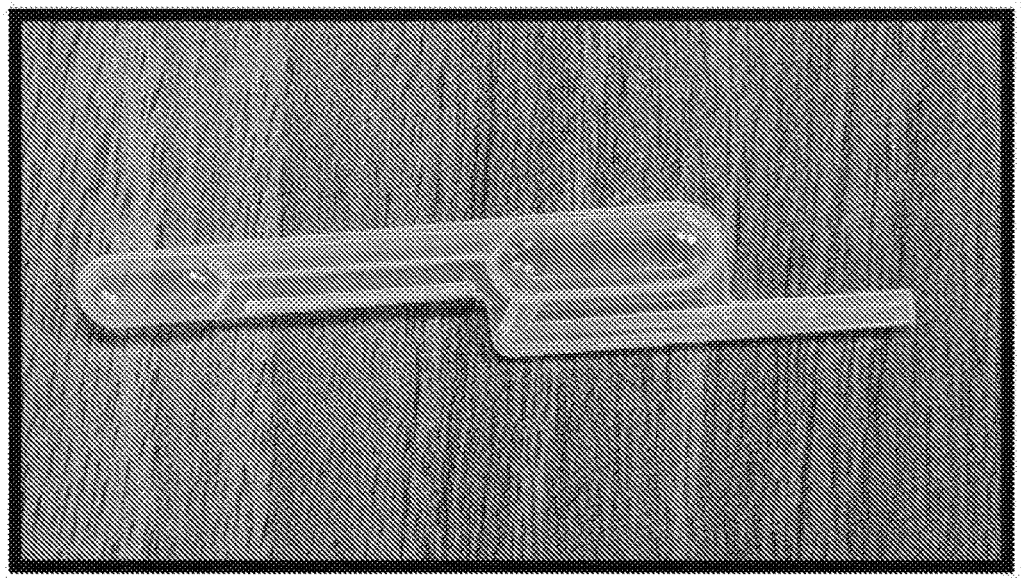
Figure 9:
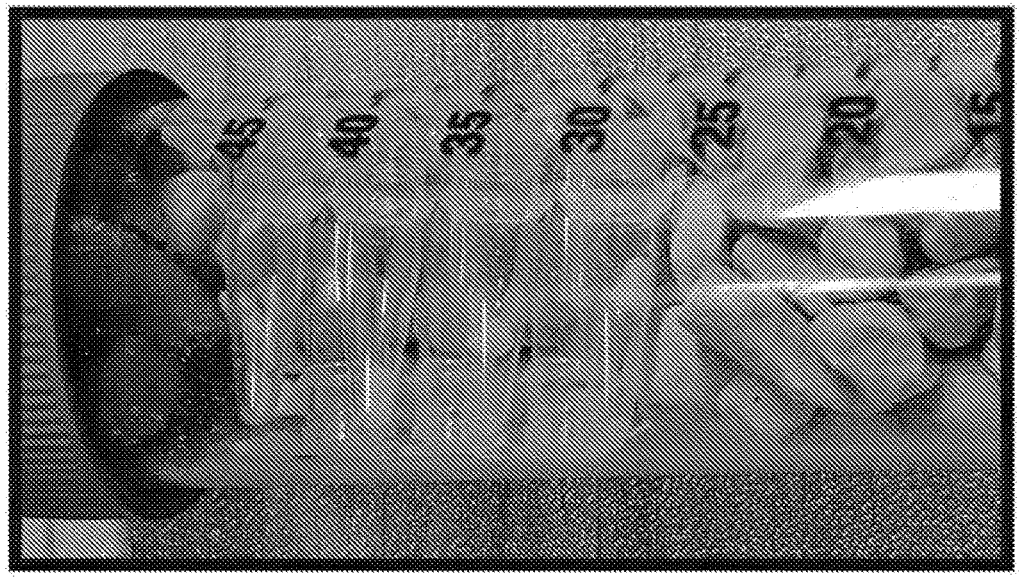

FIG. 9. Exemplary embodiments of field-testing equipment. (a) Lyophilized reactions stored in a 50 mL conical tube filled with desiccant. Reactions can be individually removed from the strip for testing on demand. Because the reactions are not stored under nitrogen gas, the tube can be opened and resealed as many times as necessary. (b) 20 μL exact volume transfer pipette (Thomas Scientific, 1207F80). Pipettes measure approximately 5 cm lengthwise. By squeezing and releasing the bulb on top, 20 μL of fluid is transferred into the stem, with any excess entering the overflow reservoir. Squeezing the bulb again dispenses the water, which is added directly to the lyophilized reactions before incubation.

Figure 10:
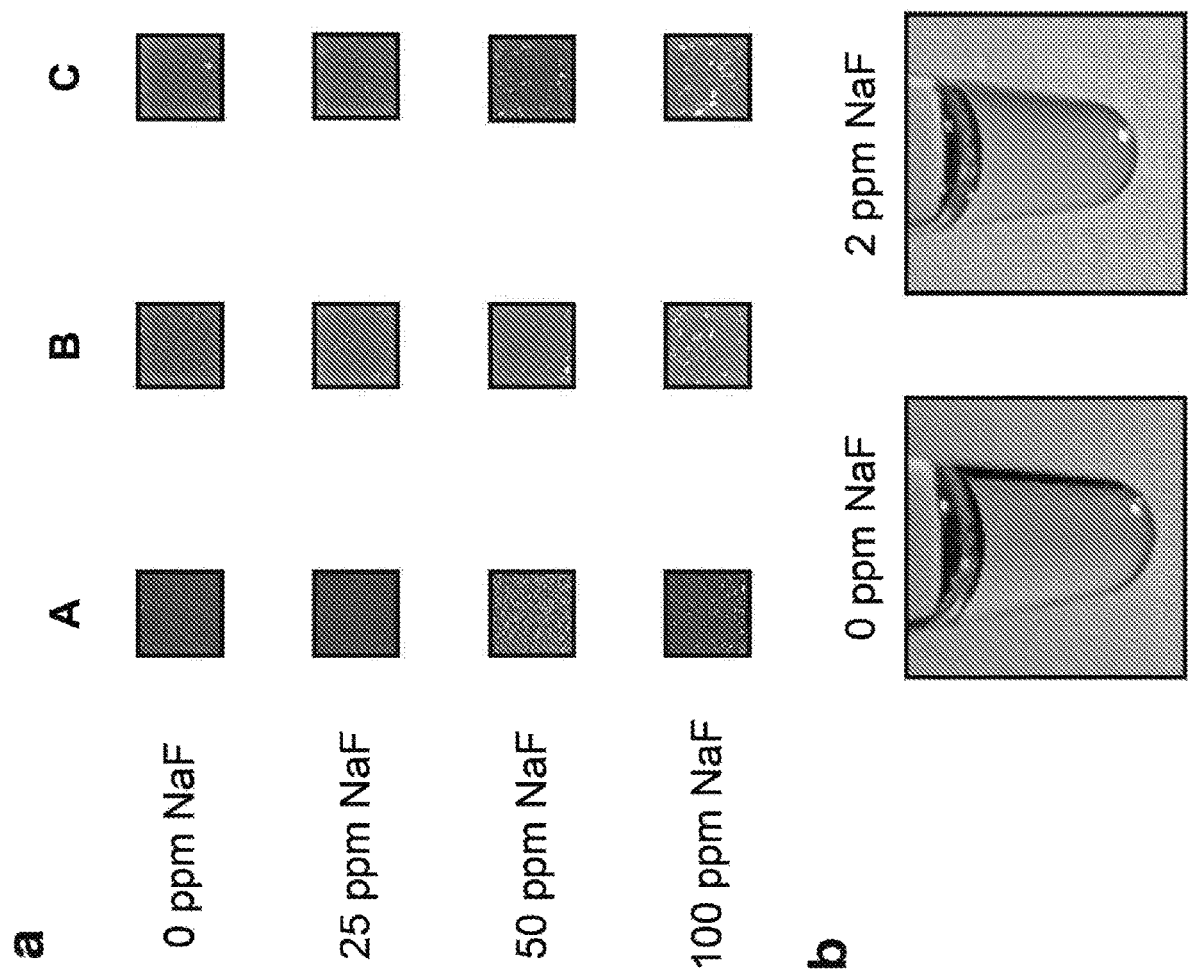

FIG. 10. The cell-free fluoride riboswitch biosensor is capable of higher-fidelity sensing than several currently available colorimetric assays. (a) Color change from three anonymized commercially available test strips with a reported sensitivity range of 10-100+ ppm of fluoride. Strips were dipped in the indicated NaF concentration in Milli-Q water and held at room temperature for 30 seconds to wait for color change, as directed by supplied instructions. No readily apparent change was observed at any fluoride concentration. (b) Fluoride detection using a cell-free reaction containing 10 nM of the fluoride riboswitch regulated C23DO DNA template. The reaction was set up, incubated at 37° C. for 1 hour, then mixed by pipetting before image capture. Despite the delayed activation due to time required for transcription and translation, clear activation (yellow color clearly discernable) can be seen at concentrations below 10 ppm.

Figure 11:
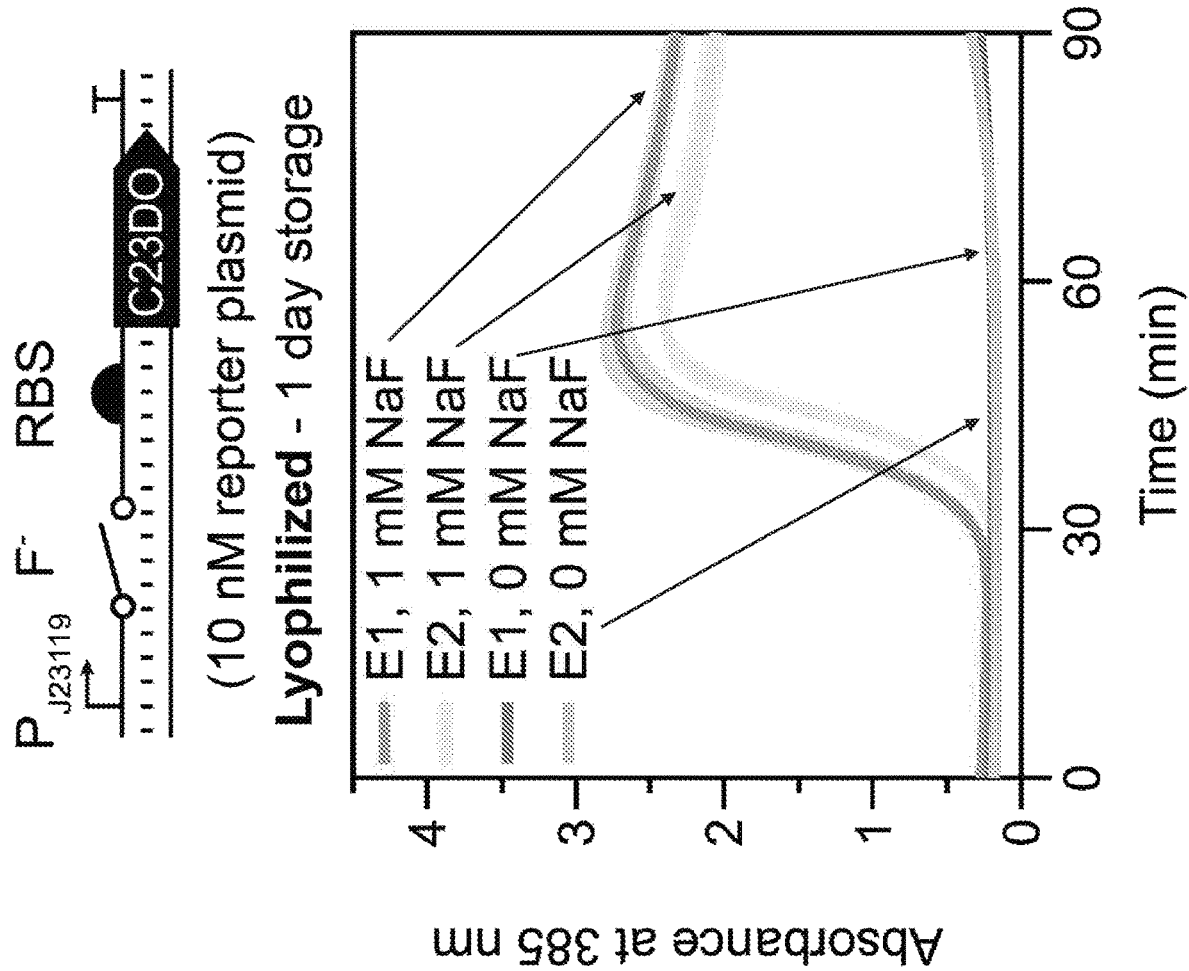

FIG. 11. Lyophilized reactions show little variability between batches of cell-free extract. Cell-free reactions containing fluoride riboswitch-regulated C23DO were set up with different batches of cell-free extract (E1 and E2) and lyophilized overnight. The next morning, reactions were rehydrated and reaction progress, read out by absorbance at 385 nm, was monitored in a plate reader maintained at 30° C. Individual time course trajectories of absorbance are marked by arrows. The reactions reached maximal activation almost simultaneously in both conditions containing 1 mM NaF (orange and yellow lines) and had negligible leak without added NaF (dark gray and light gray lines).

Figure 12:
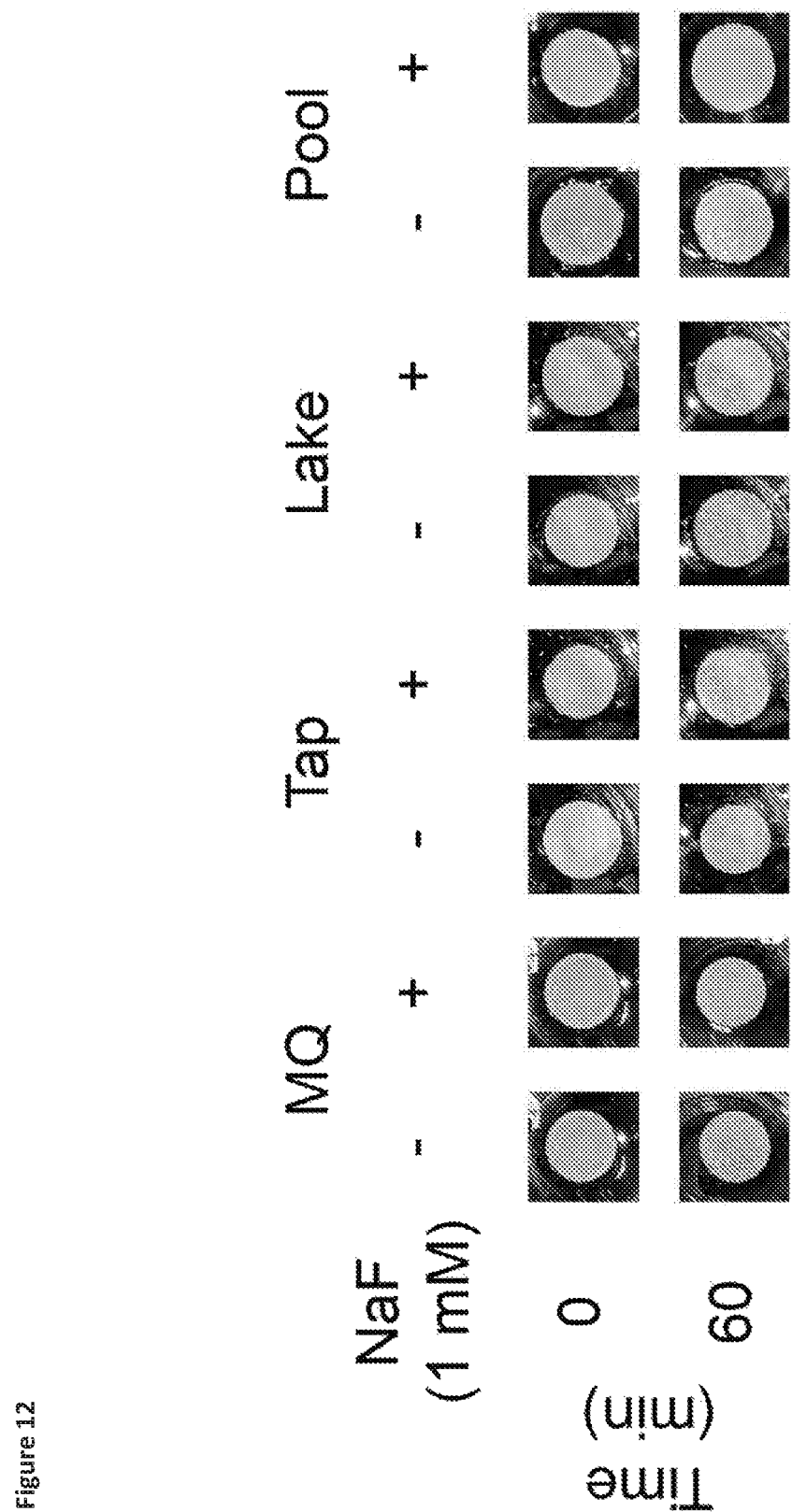

FIG. 12. Uncropped photos of lyophilized cell-free reactions on paper. Reactions pictured here are the same as those pictured in FIG. 4A. The slight pink color of some paper disks is the result of ambient lighting conditions and could not be observed by eye.

FIG. 13. Provides a table showing the sequences of constructs. Constructs utilized the Anderson promoter BBa_J23119_Spe1, the *B. cereus* crcB fluoride riboswitch, a ribosome binding site (RBS), superfolder GFP (sfGFP), catacholase 2,3 dioxygenase (C23DO), three-way junction dimeric broccoli (3wjdb), and T1/TE terminator.

FIG. 14. Provides a table showing GPS coordinates and documentation for water sampling sites depicted in FIG. 4 and FIG. 8. GPS coordinates are reported to the nearest ten minute resolution and thus represent regions sampled rather than exact locations. Measured concentrations were determined with a fluoride sensing electrode as described in Materials and Methods. "Activation" refers to the production of a visually detectable yellow color after sensor rehydration (see Materials and Methods). Data presented in FIG. 4B is from locations B and E. Permissions were received before sampling indoor faucets.

DETAILED DESCRIPTION

The presently disclosed subject matter is described herein using several definitions, as set forth below and throughout the application.

Definitions

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Unless otherwise specified or indicated by context, the terms "a", "an", and "the" mean "one or more." For example, "a component" should be interpreted to mean "one or more components."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, the terms "regulation" and "modulation" may be utilized interchangeably and may include "promotion" and "induction." For example, a switch that regulates or modulates expression of a target gene may promote and/or induce expression of expression of the target gene. In addition, the terms "regulation" and "modulation" may be utilized interchangeably and may include "inhibition" and "reduction." For example, a switch that regulates or modulates expression of a target gene may inhibit and/or reduce expression of expression of the target gene.

Ranges recited herein include the defined boundary numerical values as well as sub-ranges encompassing any non-recited numerical values within the recited range. For example, a range from about 0.01 mM to about 10.0 mM includes both 0.01 mM and 10.0 mM. Non-recited numerical values within this exemplary recited range also contemplated include, for example, 0.05 mM, 0.10 mM, 0.20 mM, 0.51 mM, 1.0 mM, 1.75 mM, 2.5 mM 5.0 mM, 6.0 mM, 7.5 mM, 8.0 mM, 9.0 mM, and 9.9 mM, among others. Exemplary sub-ranges within this exemplary range include from about 0.01 mM to about 5.0 mM; from about 0.1 mM to about 2.5 mM; and from about 2.0 mM to about 6.0 mM, among others.

The term "target molecule" means any molecule of interest in a test sample and may include so-called "small molecules" or metabolites of small molecules. A "target molecule" may include "fluoride."

As used herein, the term "sample" refers to a small or representative part or quantity from a whole or group. As used herein, a sample may be in liquid, solid or gaseous form, and may or may not include a target molecule, e.g., fluoride. In some embodiments, samples are environmental samples (e.g., removed from the environment), industrial samples (e.g., removed from a factory or industrial setting or from a region of factory, industrial, or commercial outflow), or biological samples (e.g., taken from an animal or plant). By way of example, but not by way of limitation, exemplary liquid samples include water (e.g., from ponds, springs, lakes, creeks, etc.), commercial waste effluent, and blood products. In some embodiments, solid samples may be treated with a liquid (e.g., dissolved or soaked in a liquid such as water or other solvent); likewise a gaseous sample may be exposed to or treated with a liquid prior to testing via the compositions and methods disclosed herein.

As used herein the term "reporter protein" refers to a protein that can be detected in a reaction mixture, such as a CFPS reaction mixture, typically in response to the presence of a target molecule being present in the reaction mixture. For example, a reporter protein may be expressed and detected in a CFPS reaction mixture when a target molecule such as fluoride promotes expression of the reporter protein in the CFPS reaction mixture. In some embodiments, the reporter protein comprises an enzyme, and can be detected in a reaction mixture when contacted with an appropriate substrate. Numerous reporter proteins and reporter enzyme/substrate combinations are well known in the art. By way of example, but not by way of limitation, exemplary reporter proteins include fluorescent proteins, enzymes that create colored products, and luciferase. Non-limiting examples include Green Fluorescent Protein, Red Fluorescent Protein, Yellow Fluorescent Protein, catechol 2,3-dioxygenase, lacZ, derivatives thereof, and the like.

In some embodiments, a "reporter" or "reporter molecule" comprises an RNA aptamer, such as the 3-way junction dimeric Broccoli aptamer (3WJdB). Upon transcription, 3WJdB binds 3,5-difluoro-4-hydroxybenzylidene imidazolinone (DFHBI) and activates its fluorescence. Other aptamers known in the art (e.g., Mango and Corn) would also function in the methods and compositions of the present disclosure.

The term "promoter" refers to a cis-acting DNA sequence that directs RNA polymerase and other trans-acting transcription factors to initiate RNA transcription from the DNA template that includes the cis-acting DNA sequence. By way of example, but not by way of limitation, promoters useful in the compositions and methods disclosed herein include promoters from gram positive or gram negative bacteria, or synthetic derivatives thereof. The *E. coli* Promoter BBa_J23119_Spe1, and the *E. coli* 670 promoter are two non-limiting examples.

The term "transcription factor" refers to a protein that regulates transcription of another protein, typically by interacting by one or more cis-acting DNA sequence in or near the promoter for the other protein. A transcription factor may increase expression or decrease expression depending upon whether the transcription factor is activated or deactivated. A transcription factor may become activated or deactivated by an interaction with another molecule (e.g., a target molecule as described above).

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, bacteriophage polymerases such as, but not limited to, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "riboswitch" refers to a cis-acting RNA element present in mRNA which binds a small molecule as an effector molecule, resulting in change in expression of the proteins encoded by the mRNA, either at the level of transcription or at the level of translation. Riboswitches may be divided into two parts which include an aptamer and an expression platform. The aptamer is formed by the mRNA after transcription. The aptamer then binds the effector molecule which results in structural changes in the expression platform that modulate expression of the protein encoded by the mRNA, either at the level of transcription or at the level of translation. A riboswitch thus controls expression of the protein encoded by the mRNA in response to the effector molecule. Riboswitches that are responsive to fluoride are known in the art. (See, e.g., U.S. Pat. No. 9,580,713, "Fluoride-Responsive Riboswitches, Fluoride Transporters, and Methods of Use"; the content of which is incorporated herein by reference in its entirety).

As used herein, the term "ribosome binding sequence" refers to a nucleic acid sequence that is positioned upstream of a start codon of an mRNA transcript and that is responsible for the recruitment of ribosomes during the initiation of translation. Exemplary ribosome binding sequences include, but are not limited to, the sequence shown in FIG. 13 and any other strong ribosome binding sequence; such sequences are well known in the art.

As used herein, the term "transcription terminator" refers to a nucleic acid sequence that is typically positioned at the end of a gene or an operon and that causes transcription to stop. Exemplary non-limiting transcription terminators are shown in FIG. 13 (e.g., the T1/TE terminator) and any other terminator sequence that can efficiently stop transcription from *E. coli* RNA polymerase; such sequences are well known in the art.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. As used herein, "expression template" and "transcription template" may be used interchangeably.

As used herein, "translation template" refers to an RNA product of transcription from an expression template that can be used by ribosomes to synthesize polypeptide or protein, such as mRNA.

As used herein, coupled transcription/translation ("Tx/Tl"), refers to the de novo synthesis of both RNA and a sequence defined biopolymer from the same extract. For example, coupled transcription/translation of a given sequence defined biopolymer can arise in an extract containing an expression template and a polymerase capable of generating a translation template from the expression template. Coupled transcription/translation can occur using a cognate expression template and polymerase from the organism used to prepare the extract. Coupled transcription/translation also can occur using exogenously-supplied expression template and polymerase from an orthogonal host organism different from the organism used to prepare the extract. An example of an exogenously-supplied expression template includes a translational open reading frame operably coupled a bacteriophage polymerase-specific promoter and an example of the polymerase from an orthogonal host organism includes the corresponding bacteriophage polymerase.

Proteins, Polypeptides, and Peptides

The disclosed methods, devices, kits, and components may be utilized to synthesize proteins, polypeptides, and/or peptides. As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally or non-naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

The disclosed proteins may be substantially isolated or purified. The term "substantially isolated or purified" refers to proteins that are removed from their natural environment, and are at least 60% free, preferably at least 75% free, and more preferably at least 90% free, even more preferably at least 95% free from other components with which they are naturally associated.

Polynucleotides

The disclosed methods, devices, kits, and components may utilize and/or include polynucleotides. The terms "polynucleotide," "polynucleotide sequence," "nucleic acid" and "nucleic acid sequence" refer to a nucleotide, oligonucleotide, polynucleotide (which terms may be used interchangeably), or any fragment thereof. A "polynucleotide" may refer to a polydeoxyribonucleotide (containing 2-deoxy-D-ribose), a polyribonucleotide (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs. These phrases also refer to DNA or RNA of genomic, natural, or synthetic origin (which may be single-stranded or double-stranded and may represent the sense or the antisense strand).

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, E. coli, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

"Transformation" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic host cell. The method for transformation or transfection is selected based on the type of host cell being transformed and may include, but is not limited to, bacteriophage or non-viral delivery. Methods of non-viral delivery of nucleic acids include electroporation and heat shock. The term "transformed cells" includes stably transformed cells in which the inserted DNA is capable of replication either as an autonomously replicating plasmid or as part of the host chromosome, as well as transiently transformed which express the inserted DNA or RNA for limited periods of time.

The polynucleotide sequences contemplated herein may be present in expression vectors. For example, the vectors may comprise a polynucleotide encoding an ORF of a protein. The polynucleotide present in the vector may be operably linked to a prokaryotic or eukaryotic promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter (e.g., a prokaryotic or eukaryotic promoter) operably linked to a polynucleotide that encodes a protein. A "heterologous promoter" refers to a promoter that is not the native or endogenous promoter for the protein or RNA that is being expressed. Vectors as disclosed herein may include plasmid vectors.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

Cell-Free Protein Synthesis (CFPS)

The disclosed subject matter relates in part to methods, devices, kits and components for cell-free protein synthesis. Cell-free protein synthesis (CFPS) is known and has been described in the art. (See, e.g., U.S. Pat. Nos. 6,548,276; 7,186,525; 8,734,856; 7,235,382; 7,273,615; 7,008,651; 6,994,986 U.S. Pat. Nos. 7,312,049; 7,776,535; 7,817,794; 8,298,759; 8,715,958; 9,005,920; U.S. Publication No. 2014/0349353, U.S. Publication No. 2016/0060301, U.S. Publication No. 2018/0016612, and U.S. Publication No. 2018/0016614, the contents of which are incorporated herein by reference in their entireties).

A "CFPS reaction mixture" typically contains a crude or partially-purified cell extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents. It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

An aspect of the invention is a platform for preparing a sequence defined protein in vitro which may be utilized for detecting a target molecule or metabolite thereof. The platform for preparing a sequence defined polymer or protein in vitro comprises a cellular extract from a host strain. Because CFPS exploits an ensemble of catalytic proteins prepared from the crude lysate of cells, the cell extract (whose composition is sensitive to growth media, lysis method, and processing conditions) is an important component of extract-based CFPS reactions. A variety of methods exist for preparing an extract competent for cell-free protein synthesis, including U.S. patent application Ser. No. 14/213,390 to Michael C. Jewett et al., entitled METHODS FOR CELL-FREE PROTEIN SYNTHESIS, filed Mar. 14, 2014, and now published as U.S. Patent Application Publication No. 2014/0295492 on Oct. 2, 2014, and U.S. patent application Ser. No. 14/840,249 to Michael C. Jewett et al., entitled METHODS FOR IMPROVED IN VITRO PROTEIN SYNTHESIS WITH PROTEINS CONTAINING NON STANDARD AMINO ACIDS, filed Aug. 31, 2015, and now published as U.S. Patent Application Publication No. 2016/0060301, on Mar. 3, 2016, the contents of which are incorporated by reference in its entirety.

The cellular extract of the platform may be prepared from a cell culture of a prokaryote (e.g., *E. coli*). While *E. coli* is exemplified herein, the bacterial species is not intended to be limiting. Other bacterial species suitable for the compositions and methods disclosed herein include but are not limited to (e.g., *Bacillis* species such as *Bacillus subtilis*, *Vibrio* species such as *Vibrio natrigens*, *Pseudomonas* species, etc.). In some embodiments, the cell culture is in stationary phase. In some embodiments, stationary phase may be defined as the cell culture having an OD600 of greater than about 3.0, 3.5, 4.0, 4.5, 5.0, 5.5, 6.0, 6.5, 7.0, 7.5, 8.0, or having an OD600 within a range bounded by any of these values.

The cell extract may be prepared by lysing the cells of the cell culture and isolating a fraction from the lysed cells. For example, the cell extract may be prepared by lysing the cells of the cell culture and subjecting the lysed cells to centrifugal force, and isolating a fraction after centrifugation (e.g., where the S12 fraction and/or S30 fraction is isolated).

The platform may comprise an expression template, a translation template, or both an expression template and a translation template. The expression template serves as a substrate for transcribing at least one RNA that can be translated into a sequence defined biopolymer (e.g., a polypeptide or protein). The translation template is an RNA product that can be used by ribosomes to synthesize the sequence defined biopolymer. In certain embodiments the platform comprises both the expression template and the translation template. In certain specific embodiments, the platform may be a coupled transcription/translation ("Tx/Tl") system where synthesis of translation template and a sequence defined biopolymer from the same cellular extract.

The platform may comprise one or more polymerases capable of generating a translation template from an expression template. The polymerase may be supplied exogenously or may be supplied from the organism used to prepare the extract. In certain specific embodiments, the polymerase is expressed from a plasmid present in the organism used to prepare the extract and/or an integration site in the genome of the organism used to prepare the extract.

Altering the physicochemical environment of the CFPS reaction to better mimic the cytoplasm can improve protein synthesis activity. The following parameters can be considered alone or in combination with one or more other components to improve robust CFPS reaction platforms based upon crude cellular extracts (for examples, S12, S30 and S60 extracts).

The temperature may be any temperature suitable for CFPS. Temperature may be in the general range from about 10° C. to about 40° C., including intermediate specific ranges within this general range, include from about 15° C. to about 35° C., from about 15° C. to about 30° C., from about 15° C. to about 25° C. In certain aspects, the reaction temperature can be about 15° C., about 16° C., about 17° C., about 18° C., about 19° C., about 20° C., about 21° C., about 22° C., about 23° C., about 24° C., about 25° C.

The CFPS reaction can include any organic anion suitable for CFPS. In certain aspects, the organic anions can be glutamate, acetate, among others. In certain aspects, the concentration for the organic anions is independently in the general range from about 0 mM to about 200 mM, including intermediate specific values within this general range, such as about 0 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM and about 200 mM, among others.

The CFPS reaction can also include any halide anion suitable for CFPS. In certain aspects the halide anion can be chloride, bromide, iodide, among others. A preferred halide anion is chloride. Generally, the concentration of halide anions, if present in the reaction, is within the general range from about 0 mM to about 200 mM, including intermediate specific values within this general range, such as those disclosed for organic anions generally herein.

The CFPS reaction may also include any organic cation suitable for CFPS. In certain aspects, the organic cation can be a polyamine, such as spermidine or putrescine, among others. Preferably polyamines are present in the CFPS reaction. In certain aspects, the concentration of organic cations in the reaction can be in the general about 0 mM to about 3 mM, about 0.5 mM to about 2.5 mM, about 1 mM to about 2 mM. In certain aspects, more than one organic cation can be present.

The CFPS reaction can include any inorganic cation suitable for CFPS. For example, suitable inorganic cations can include monovalent cations, such as sodium, potassium, lithium, among others; and divalent cations, such as magnesium, calcium, manganese, among others. In certain aspects, the inorganic cation is magnesium. In such aspects, the magnesium concentration can be within the general range from about 1 mM to about 50 mM, including intermediate specific values within this general range, such as about 1 mM, about 2 mM, about 3 mM, about 5 mM, about 6 mM, about 7 mM, about 8 mM, about 9 mM, about 10 mM, among others. In preferred aspects, the concentration of inorganic cations can be within the specific range from about 4 mM to about 9 mM and more preferably, within the range from about 5 mM to about 7 mM.

The CFPS reaction includes NTPs. In certain aspects, the reaction uses ATP, GTP, CTP, and UTP. In certain aspects, the concentration of individual NTPs is within the range from about 0.1 mM to about 2 mM.

The CFPS reaction can also include any alcohol suitable for CFPS. In certain aspects, the alcohol may be a polyol, and more specifically glycerol. In certain aspects the alcohol is between the general range from about 0% (v/v) to about 25% (v/v), including specific intermediate values of about 5% (v/v), about 10% (v/v) and about 15% (v/v), and about 20% (v/v), among others.

Expression Cassettes

The disclosed methods and systems may utilize and/or include one or more expression cassettes which alternatively may be referred to as transcription templates. The disclosed methods and systems typically utilize and/or include an expression cassette comprising one or more of the following components: (i) a promoter (e.g., a synthetic constitutive *E. coli* Promoter BBa_J23119_Spe1, to drive strong transcription and/or a T7 promoter); (ii) a fluoride-sensing riboswitch (e.g., the *Bacillus cereus* fluoride riboswitch sequence, which induces transcription based on the presence of fluoride); (iii) a ribosome binding sequence (e.g., a synthetic ribosome binding site to drive strong translation); (iv) an encoded reporter (e.g. the coding sequence for an enzyme such catechol 2,3-dioxygenase or a fluorescent protein such as GFP or a derivative thereof) and; (v) a transcription terminator (e.g., the T1/TE double transcriptional terminator). An expression cassette comprising the one or more components may be utilized to sense fluoride in a cell-free gene expression reaction, wherein the reaction comprises metabolism from a host strain that (i) provides energy; (ii) provides cofactor regeneration; (iii) provides enzymes used for cell-free sensing; or (iv) any combination thereof as well as exogenously supplied cell-free protein synthesis reagents and an RNA polymerase.

Also disclosed are vectors comprising the disclosed expression cassettes. Suitable vectors may include episomal vectors such as plasmid vectors.

Also disclosed are cells comprising the disclosed expression cassettes, optionally where the expression cassettes are present in the cells as one or more episomal vectors such as episomal plasmids. Exemplary cells may include prokaryotic cells, include bacteria suitable for large-scale production methods.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Illustrative Embodiments

The following illustrative embodiments are exemplary, and are not intended to limit the scope of the claims.

Embodiment 1. A method of detecting fluoride in a sample, optionally wherein the sample is an environmental sample, an industrial sample, and/or a biological sample, the method comprising: (i) obtaining an environmental sample or biological sample which may or may not contain fluoride; (ii) adding the sample to a cell-free protein synthesis (CFPS) reaction, wherein if fluoride is present in the sample then a detectable output is generated (e.g., a visual, electronic, or optical output).

Embodiment 2. The method of embodiment 1, wherein the detectable output is generated if fluoride is present in the environmental sample or biological sample at a concentration less than about 10.0, 1.0 mM, 0.5 mM, 0.1 mM, 0.05 mM, or 0.01 mM.

Embodiment 3. The method of embodiment 1 or 2, wherein the detectable output is generated within less than about 300, 240, 180, 120, 90, 60, 40, 30, 20, or 10 minutes, if fluoride is present in the environmental sample or biological sample at a concentration less than about 10.0 mM, 1.0 mM, 0.5 mM, 0.1 mM, 0.05 mM, or 0.01 mM.

Embodiment 4. The method of any of the foregoing embodiments, wherein the CFPS reaction comprises: (a) a cell extract from a host strain that provides and/or regenerates one or more of: (i) energy; (ii) cofactors; (iii) enzymes used for cell-free sensing of the target molecule; or (iv) any combination thereof; and (b) exogenous supplied cell-free protein synthesis reagents not present in the cell extract that comprise at least one expression cassette and/or a polymerase.

Embodiment 5. The method of embodiment 4, wherein the expression cassette comprises one or more of the following components: (i) a promoter (e.g., a synthetic constitutive E. coli Promoter BBa_J23119_Spe1, to drive strong transcription and/or a T7 promoter); (ii) a fluoride-sensing riboswitch (e.g., the Bacillus cereus fluoride riboswitch sequence, which induces transcription based on the presence of fluoride); (iii) a ribosome binding sequence (e.g., a synthetic ribosome binding site to drive strong translation); (iv) an encoded reporter (e.g. the coding sequence for an enzyme such as catechol 2,3-dioxygenase and/or a fluorescent protein such as GFP or a derivative thereof and/or an RNA aptamer and/or a cognate fluorophore); and/or (v) a transcription terminator (e.g., the T1/TE double transcriptional terminator).

Embodiment 6. The method of any of the foregoing embodiments, wherein the visual, electronic, or optical output is generated by a reporter that is expressed in the CFPS reaction in the presence of fluoride.

Embodiment 7. The method of embodiment 6, wherein the visual, electronic, or optical output is generated from an enzymatic reaction catalyzed by the reporter protein, optionally wherein the reporter is catechol 2,3-dioxygenase and the CFPS further comprises a colorimetric substrate for catechol 2,3-dioxygenase such as catechol.

Embodiment 8. The method of embodiment 6, wherein the reporter is a fluorescent protein, optionally wherein the fluorescent protein is GFP or a derivative thereof.

Embodiment 9. The method of embodiment 6, wherein the reporter is a fluorogenic or colorimetric RNA aptamer, optionally wherein the fluorogenic aptamer is a 3-Way Junction Dimeric Broccoli aptamer and the CFPS further comprises a colorimetric substrate for the aptamer.

Embodiment 10. The method of any of the foregoing embodiments, wherein the optical output is luminescence, fluorescence, or visible color.

Embodiment 11. A device or kit comprising components for detecting a target molecule according to any of the previous embodiments, wherein the components comprise preserved CFPS reaction components, optionally wherein the preserved CFPS reaction components are preserved by freeze-drying.

Embodiment 12. The device or kit of embodiment 11, wherein the preserved CFPS reaction components are supported on a substrate which optionally is a paper substrate (e.g., a paper test article).

Embodiment 13. The device or kit of embodiment 11 or 12, wherein the substrate (optionally the paper support such as a paper test article) comprises components that are preserved by freeze-drying.

Embodiment 14. The device or kit of any of embodiments 11-1, further comprising a component for reading an electronic, optical, or fluorescent output.

Embodiment 15. An expression cassette comprising one or more of the following components: (i) a promoter (e.g., a synthetic constitutive E. coli Promoter BBa_J23119_Spe1, to drive strong transcription and/or a T7 promoter); (ii) a fluoride-sensing riboswitch (e.g., the Bacillus cereus fluoride riboswitch sequence, which induces transcription based on the presence of fluoride); (iii) a ribosome binding sequence (e.g., a synthetic ribosome binding site to drive strong translation); (iv) an encoded reporter (e.g. the coding sequence for an enzyme such as catechol 2,3-dioxygenase or a fluorescent protein such as GFP or a derivative thereof); and/or (v) a transcription terminator (e.g., the T1/TE double transcriptional terminator).

Embodiment 16. A platform for detecting fluoride in an environmental or biological sample, the platform comprising: (i) components for performing a cell-free protein synthesis (CFPS) reaction; and (ii) the expression cassette of illustrative embodiment 15.

Embodiment 17. The platform of embodiment 16, wherein the encoded reporter is an enzyme (e.g., catechol 2,3-dioxygenase) that catalyzes conversion of a substrate (e.g., catechol) to a detectable product and the platform further comprises the substrate for the enzyme.

Embodiment 18. The platform of embodiment 16, wherein the encoded reporter is a fluorescent protein, optionally wherein the fluorescent protein is GFP or a derivative thereof.

Embodiment 19. The platform of claim 16, wherein the reporter is a fluorogenic RNA aptamer, optionally wherein the fluorogenic aptamer is a 3-Way Junction Dimeric Broccoli aptamer and the CFPS further comprises a colorimetric substrate for the aptamer.

Embodiment 20. The platform of any of embodiments 16-19, wherein the components for performing a cell-free protein synthesis (CFPS) reaction comprise at least a cell-free extract, optionally a cell-free extract prepared from *E. coli*.

EXAMPLES

The following Examples are illustrative and are not intended to limit the scope of the claimed subject matter.

Example 1—Riboswitch-Based Fluoride Sensing in Cell-Free Extract

Abstract

Advances in biosensor engineering have enabled the creation of programmable genetic systems for the detection of a range of pathogens, nucleic acids, and small molecules. However, existing detection strategies require extensive optimization and rely on the availability of characterized transcription factors for a target of interest. Disclosed is a genetically encoded system for molecular sensing based on a functional RNA sequence ("riboswitch") responsive to target molecules in cell-free extract. Methods specific for detecting and identifying the presence of fluoride are also provided.

Description of Technology

This invention constitutes the sensing of molecules in a bacterial extract-based cell-free gene expression reaction with a fluorescent or colorimetric reporter readout. This sensing is accomplished through a functional RNA sequence ("riboswitch") responding to its target ligand to regulate expression of a fluorescent or colorimetric reporter. The full reaction can be freeze-dried and reconstituted with the liquid sample either in tubes, well-plates, or immobilized on a paper substrate.

In an embodiment, the fluoride-sensing genetic construct includes five components placed in sequence: (i) Synthetic constitutive *E. coli* Promoter BBa_J23119_Spe1, to drive strong transcription; (ii) the *Bacillus cereus* fluoride riboswitch sequence, which permits or prohibits transcription based on the presence of fluoride; (iii) a synthetic ribosome binding sequence, to drive strong translation; (iv) the coding sequence for a colorimetric (catechol 2,3-dioxygenase) reporter and; (v) the T1/TE double transcriptional terminator. A DNA construct encoding those pieces is used to sense fluoride in a cell-free gene expression reaction, wherein the reaction comprises metabolism from the host strain that (i) provides energy; (ii) provides cofactor regeneration; (iii) provides enzymes used for cell-free sensing; or (iv) any combination thereof as well as exogenously supplied cell-free protein synthesis reagents, at least one transcription template (the DNA construct), and an RNA polymerase.

Extracts for cell-free protein synthesis were prepared as described in "Deconstructing Cell-Free Extract Preparation for in Vitro Activation of Transcriptional Genetic Circuitry" (Silverman et al, 2018, herein incorporated by reference in its entirety). This differs from other platforms using the PUREsystem and its variants (e.g. NEB PURExpress) in that it is a whole cell extract, rather than an expression system reconstituted from individually purified transcriptional and translational components. Furthermore, the extract is processed after cell lysis via incubation and dialysis steps. This post lysis processing of the extract enables the use of native *E. coli* transcriptional machinery, which is required for riboswitches function—i.e. riboswitches are non-functional in the unprocessed extracts used in existing technologies.

The use of a functional RNA to sense small molecule targets also differs from existing RNA biosensing technologies, which are focused on nucleic acid detection. Because of the reduced expression levels from *E. coli* polymerase compared to T7 polymerase and the relatively poor binding of the riboswitch to fluoride, fluorescent reporters do not produce a strong enough signal for detection. However, with the increased sensitivity via the amplification provided by an enzymatic colorimetric reporter, even low levels of expression result in the complete conversion of substrate and production of a visually detectable output, enabling the application of the *B. cereus* fluoride riboswitch as a practical biosensor.

For sample detection, cell-free protein synthesis reactions are lyophilized and rehydrated with an environmental sample which may or may not contain fluoride. In the reaction, the presence of fluoride allows the riboswitch to preferentially adopt a conformation that permits transcription of the downstream reporter. The presence of the fluoride can then be determined via the induction of a visually detectable colorimetric output.

Applications

Applications of the disclosed technology include, but are not limited to: ((i) On-demand biosensing of molecules using colorimetric reporters; (ii) Lyophilization and reconstitution of these biosensors and/or immobilization on a fibrous substrate; (iii) Real-time detection of toxins and/or contaminants in biological or environmental samples; and (iv) Point-of-care diagnostics in biological samples.

Advantages

Advantages of the disclosed technology include, but are not limited to: (i) Faster, more portable, and less expensive than existing chemical, electrochemical, or analytical processes for detecting environmental contaminants or other analytes of interest; (ii) Enables rapid visible detection of target molecules over background using colorimetric measurement; and (iii) Compared to whole-cell biosensors, little-to-no concern for biocontainment or regulations on transgenic organisms, issues with ligand permeability or degradation inside cells, or cytotoxicity; (iv) Consists of one regulatory component (riboswitch) instead of multiple (transcription factor and operator sites), simplifying optimization; and (v) Can sense targets lacking well-characterized transcription factors, i.e., fluoride.

NON-PATENT REFERENCES

1. Organization, W. H. World health statistics 2016: monitoring health for the SDGs sustainable development goals. (World Health Organization, 2016).
2. Onda, K., LoBuglio, J. & Bartram, J. Global access to safe water: accounting for water quality and the resulting impact on MDG progress. Int. J. Environ. Res. Public Health 9, 880-894 (2012).
3. Edition, F. Guidelines for drinking-water quality. WHO Chron. 38, 104-108 (2011).

4. Maheshwari, R. C. Fluoride in drinking water and its removal. J. Hazard. Mater. 137, 456-463 (2006).
5. Krishnamachari, K. A. Skeletal fluorosis in humans: a review of recent progress in the understanding of the disease. Prog. Food Nutr. Sci. 10, 279-314 (1986).
6. Schmidt, C. M. & Smolke, C. D. RNA Switches for Synthetic Biology. Cold Spring Harb. Perspect. Biol. 11, (2019).
7. Mandal, M. & Breaker, R. R. Gene regulation by riboswitches. Nat. Rev. Mol. cell Biol. 5, 451 (2004).
8. Berens, C. & Suess, B. Riboswitch engineering-making the all-important second and third steps. Curr. Opin. Biotechnol. 31, 10-15 (2015).
9. Ogawa, A. Rational design of artificial riboswitches based on ligand-dependent modulation of internal ribosome entry in wheat germ extract and their applications as label-free biosensors. RNA (2011).
10. McCown, P. J., Corbino, K. A., Stav, S., Sherlock, M. E. & Breaker, R. R. Riboswitch diversity and distribution. Rna 23, 995-1011 (2017).
11. Baker, J. L. et al. Widespread genetic switches and toxicity resistance proteins for fluoride. Science (80-.). 335, 233-235 (2012).
12. Watters, K. E., Strobel, E. J., Angela, M. Y., Lis, J. T. & Lucks, J. B. Cotranscriptional folding of a riboswitch at nucleotide resolution. Nat. Struct. Mol. Biol. 23, 1124 (2016).
13. Ren, A., Rajashankar, K. R. & Patel, D. J. Fluoride ion encapsulation by Mg 2+ ions and phosphates in a fluoride riboswitch. Nature 486, 85 (2012).
14. Selifonova, O., Burlage, R. & Barkay, T. Bioluminescent sensors for detection of bioavailable Hg (II) in the environment. Appl. Environ. Microbiol. 59, 3083-3090 (1993).
15. Tauriainen, S., Karp, M., Chang, W. & Virta, M. Luminescent bacterial sensor for cadmium and lead. Biosens. Bioelectron. 13, 931-938 (1998).
16. Pardee, K. et al. Paper-Based Synthetic Gene Networks. Cell 159, 940-954 (2014).
17. Pardee, K. et al. Rapid, low-cost detection of Zika virus using programmable biomolecular components. Cell 165, 1255-1266 (2016).
18. Carlson, E. D., Gan, R., Hodgman, C. E. & Jewett, M. C. Cell-free protein synthesis: applications come of age. Biotechnol. Adv. 30, 1185-1194 (2012).
19. Hodgman, C. E. & Jewett, M. C. Cell-free synthetic biology: thinking outside the cell. Metab. Eng. 14, 261-269 (2012).
20. Kelley, S. O. et al. Advancing the speed, sensitivity and accuracy of biomolecular detection using multi-length-scale engineering. Nat. Nanotechnol. 9, 969 (2014).
21. Etzel, M. & Morl, M. Synthetic Riboswitches: From Plug and Pray toward Plug and Play. Biochemistry 56, 1181-1198 (2017).
22. Zadeh, J. N. et al. NUPACK: analysis and design of nucleic acid systems. J. Comput. Chem. 32, 170-173 (2011).
23. Alam, K. K., Tawiah, K. D., Lichte, M. F., Porciani, D. & Burke, D. H. A Fluorescent Split Aptamer for Visualizing RNA-RNA Assembly In Vivo. ACS Synth. Biol. 6, 1710-1721 (2017).
24. Chappell, J., Westbrook, A., Verosloff, M. & Lucks, J. B. Computational design of small transcription activating RNAs for versatile and dynamic gene regulation. Nat. Commun. 8, 1051 (2017).
25. Verosloff, M., Chappell, J., Perry, K. L., Thompson, J. R. & Lucks, J. B. PLANT-Dx: A Molecular Diagnostic for Point of Use Detection of Plant Pathogens. bioRxiv 498998 (2018). doi:10.1101/498998
26. Haklay, M. & Weber, P. Openstreetmap: User-generated street maps. Ieee Pervas Comput 7, 12-18 (2008).
27. F, R., G, F., E, M., Martinez Cruz, M. & Bergen M. J., van. Fluorosis dental en la poblaciòn infantil en las cercanias del volcàn Irazù, Costa Rica. (2014).
28. Mascarenhas, A. K. Risk factors for dental fluorosis: a review of the recent literature. Pediatr. Dent. 22, 269-277 (2000).
29. Calhoun, K. A. & Swartz, J. R. in (ed. Grandi, G.) 3-17 (Humana Press, 2007). doi:10.1007/978-1-59745-388-2_1
30. Salehi, A. S. M. et al. Cell-free protein synthesis approach to biosensing hTRβ-specific endocrine disruptors. Anal. Chem. 89, 3395-3401 (2017).
31. Takahashi, M. K. et al. A low-cost paper-based synthetic biology platform for analyzing gut microbiota and host biomarkers. Nat. Commun. 9, 3347 (2018).
32. Stark, J. C. et al. BioBits™ Bright: A fluorescent synthetic biology education kit. Sci. Adv. 4, eaat5107 (2018).
33. Huang, A. et al. BioBits™ Explorer: A modular synthetic biology education kit. Sci. Adv. 4, eaat5105 (2018).
34. Hu, C. Y., Varner, J. D. & Lucks, J. B. Generating Effective Models and Parameters for RNA Genetic Circuits. ACS Synth. Biol. 4, 914-926 (2015).
35. Travascio, P., Bennet, A. J., Wang, D. Y. & Sen, D. A ribozyme and a catalytic DNA with peroxidase activity: active sites versus cofactor-binding sites. Chem. Biol. 6, 779-787 (1999).
36. Silverman, A., Kelley-Loughnane, N., Lucks, J. B. & Jewett, M. C. Deconstructing cellfree extract preparation for in vitro activation of transcriptional genetic circuitry. ACS Synth. Biol. (2018). doi:10.1021/acssynbio.8b00430.
37. Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
38. Jewett, M. C. & Swartz, J. R. Mimicking the *Escherichia coli* cytoplasmic environment activates long-lived and efficient cell-free protein synthesis. Biotechnology and bioengineering 86, 19-26, doi:10.1002/bit.20026 (2004).
39. Caschera, F. & Noireaux, V. Synthesis of 2.3 mg/ml of protein with an all *Escherichia coli* cell-free transcription-translation system. Biochimie 99, 162-168, doi:10.1016/j.biochi.2013.11.025 (2014).
40. Zawada, J. F. et al. Microscale to manufacturing scale-up of cell-free cytokine production—a new approach for shortening protein production development timelines. Biotechnology and bioengineering 108, 1570-1578, doi:10.1002/bit.23103 (2011).
41. Hong, S. H. et al. Improving Cell-Free Protein Synthesis through Genome Engineering of *Escherichia coli* Lacking Release Factor 1. Chembiochem: a European journal of chemical biology, doi:10.1002/cbic.201402708 (2015).
42. Yang, W. C. et al. Cell-free production of transducible transcription factors for nuclear reprogramming. Biotechnology and bioengineering 104, 1047-1058, doi:10.1002/bit.22517 (2009).
43. Chappell, J., Jensen, K. & Freemont, P. S. Validation of an entirely in vitro approach for rapid prototyping of DNA regulatory elements for synthetic biology. Nucleic acids research 41, 3471-3481, doi:10.1093/nar/gkt052 (2013).

44. Karim, A. S. & Jewett, M. C. A cell-free framework for rapid biosynthetic pathway prototyping and enzyme discovery. Metabolic engineering 36, 116-126, doi:10.1016/j.ymben.2016.03.002 (2016).
45. Shin, J. & Noireaux, V. An E. coli cell-free expression toolbox: application to synthetic gene circuits and artificial cells. ACS synthetic biology 1, 29-41, doi:10.1021/sb200016s (2012).
46. Studier, F. W. & Moffatt, B. A. Use of bacteriophage T7 RNA polymerase to direct selective high-level expression of cloned genes. Journal of molecular biology 189, 113-130 (1986).
47. Kwon, Y. C. & Jewett, M. C. High-throughput preparation methods of crude extract for robust cell-free protein synthesis. Scientific reports 5, 8663, doi:10.1038/srep08663 (2015).
48. Swartz, J. R., Jewett, M. C. & Woodrow, K. A. Cell-free protein synthesis with prokaryotic combined transcription-translation. Methods in molecular biology (Clifton, N.J.) 267, 169-182, doi:10.1385/1-59259-774-2:169 (2004).
49. Wen, K. Y., et al., A Cell-Free Biosensor for Detecting Quorum Sensing Molecules in P. aeruginosa-Infected Respiratory Samples. ACS Synthetic Biology, 2017. 6(12): p. 2293-2301.
50. Sun, Z. Z., et al., Protocols for Implementing an Escherichia coli Based TX-TL Cell-Free Expression System for Synthetic Biology. 2013(79): p. e50762.
51. Pardee, K., et al. "Paper-Based Synthetic Gene Networks." Cell 159(4): 940-954.
52. Jia, K., et al., A lower limit of detection for atrazine was obtained using bioluminescent reporter bacteria via a lower incubation temperature. Ecotoxicology and Environmental Safety, 2012. 84: p. 221-226
53. Hua, A., et al., Development of a bacterial bioassay for atrazine and cyanuric acid detection. Frontiers in Microbiology, 2015. 6: p. 211
54. Garcia-Gonzàlez, V., et al., Regulation of the Pseudomonas sp. Strain ADP Cyanuric Acid Degradation Operon. Journal of Bacteriology, 2005. 187(1): p. 155-167.
55. Baker, Jenny L., et al. "Widespread genetic switches and toxicity resistance proteins for fluoride." Science 335.6065 (2012): 233-235.
56. Muranaka, Norihito, et al. "Efficient design strategy for whole-cell and cell-free biosensors based on engineered riboswitches." Analytical Letters 42.1 (2009): 108-122.
57. Silverman, Adam D., et al. "Deconstructing Cell-Free Extract Preparation for in Vitro Activation of Transcriptional Genetic Circuitry." ACS Synthetic Biology (2018) DOI:10.1021/acssynbio.8b00430; the contents of which are incorporated herein by reference in their entireties.

PATENT REFERENCES

U.S. Pat. Nos.: U.S. Pat. Nos. 5,478,730; 5,556,769; 5,665,563; 6,168,931; 6,518,058; 6,783,957; 6,869,774; 6,994,986; 7,118,883; 7,189,528; 7,338,789; 7,387,884; 7,399,610; 8,357,529; 8,574,880; 8,703,471; 8,999,668; 9,410,170; US952813; U.S. Pat. No. 9,580,713, "Fluoride-Responsive Riboswitches, Fluoride Transporters, and Methods of Use"; the contents of which are incorporated herein by reference in their entirety.
U.S. Patent Publications: US20040209321; US20050170452; US20060211085; US20060234345; US20060252672; US20060257399; US20060286637; US20070026485; US20070154983; US20070178551; US20080138857; US20140295492; US20160060301; US20180016612; US20180016614; US20160312312; and US20160362708; the contents of which are incorporated herein by reference in their entirety.
Published International Applications: WO2003056914A1; WO2004013151A2; WO2004035605A2; WO2006102652A2; WO2006119987A2; WO2007120932A2; WO2014144583; WO2017117539; and WO 2017/031399, "Compositions and multiplexed systems for coupled cell-free transcription-translation and protein synthesis and method for using them"; the contents of which are incorporated herein by reference in their entirety.

Example 2—Design and Field Deployment of Cell-Free Riboswitch-Based Fluoride Biosensor Abstract Advances in biosensor engineering have enabled the design of programmable molecular systems to detect a range of pathogens, nucleic acids, and chemicals. Here, we engineer and field-test a biosensor for fluoride, a major groundwater contaminant of global concern. The sensor consists of a cell-free system containing a DNA template that encodes a fluoride-responsive riboswitch regulating genes that produce a fluorescent or colorimetric output. Individual reactions can be lyophilized for long-term storage and detect fluoride at levels above 2 parts per million, the Environmental Protection Agency's most stringent regulatory standard, in both laboratory and field conditions. Through onsite detection of fluoride in a real-world water source, this work provides a critical proof-of-principle for the future engineering of riboswitches and other biosensors to address challenges for global health and the environment.

Introduction

Safe drinking water availability is an important contributor to public welfare[1]. However, safe water sources are not available to a large portion of the globe, with an estimated 3 billion people using water from either an unsafe source or a source with significant sanitary risks[2]. One particularly dangerous contaminant is fluoride, which leaches into groundwater from natural sources. Long-term exposure to fluoride concentrations above 2 parts per million (ppm) can cause dental and skeletal fluorosis, heavily burdening communities in resource-limited settings[3]. Though large-scale remediation strategies are available, they are resource-intensive and difficult to deploy[3,4]. This problem is compounded by the reliance of gold-standard sensing methods on expensive analytical equipment, making detection difficult in areas with the greatest need[4]. While many emerging fluorescent and colorimetric chemical fluoride sensors exist, these either require supplementary imaging equipment or utilize toxic organic solvents, hampering their use in real-world conditions[5]. To facilitate targeted remediation and empower affected individuals, there is a pressing need for a more practical, rapid, and field-deployable solution to monitor the presence of fluoride in water.

Because they can be lyophilized and rehydrated on-demand, cell-free expression (CFE) systems have recently become a promising platform for field-deployable molecular diagnostics[6-9]. These systems typically consist of cellular gene expression machinery along with the required buffers, energy sources and co-factors necessary to support gene expression from added DNA templates[10]. Unlike whole cells, cell-free platforms offer an open, easily tunable reaction environment, expediting the design process for genetically encoded programs[10]. Furthermore, they circumvent the analyte toxicity, host mutation, and biocontainment concerns limiting cellular sensors[11].

We sought to leverage the advantages of cell-free biosensing platforms to create a new approach for monitoring for the presence of fluoride in water using a fluoride-responsive riboswitch that regulates the expression of the CrcB fluoride efflux pump in Bacillus cereus[12]. By configuring the B. cereus crcB fluoride riboswitch to control the transcription of downstream reporter genes[13], we show that a cell-free gene expression system can activate both protein and RNA reporter expression in the presence of fluoride. With an enzymatic colorimetric reporter, we demonstrate detection of fluoride concentrations at the Environmental Protection Agency (EPA) Secondary Maximum Contaminant Level of 2 ppm[14]. Notably, these cell-free biosensors showed more accurate sensing with a lower limit of detection than several tested commercially available consumer fluoride testing kits. We also demonstrate that our fluoride biosensor can be lyophilized for long-term storage and distribution, allowing us to detect fluoride in unprocessed groundwater obtained and tested onsite in Costa Rica. This work exemplifies the potential of riboswitches as practical biosensing tools and helps lay the foundation for utilizing cell-free biosensing systems in rapid and field-deployable water quality diagnostics to address pressing challenges in global health.

A. Initial Development and Characterization

Figure 1:
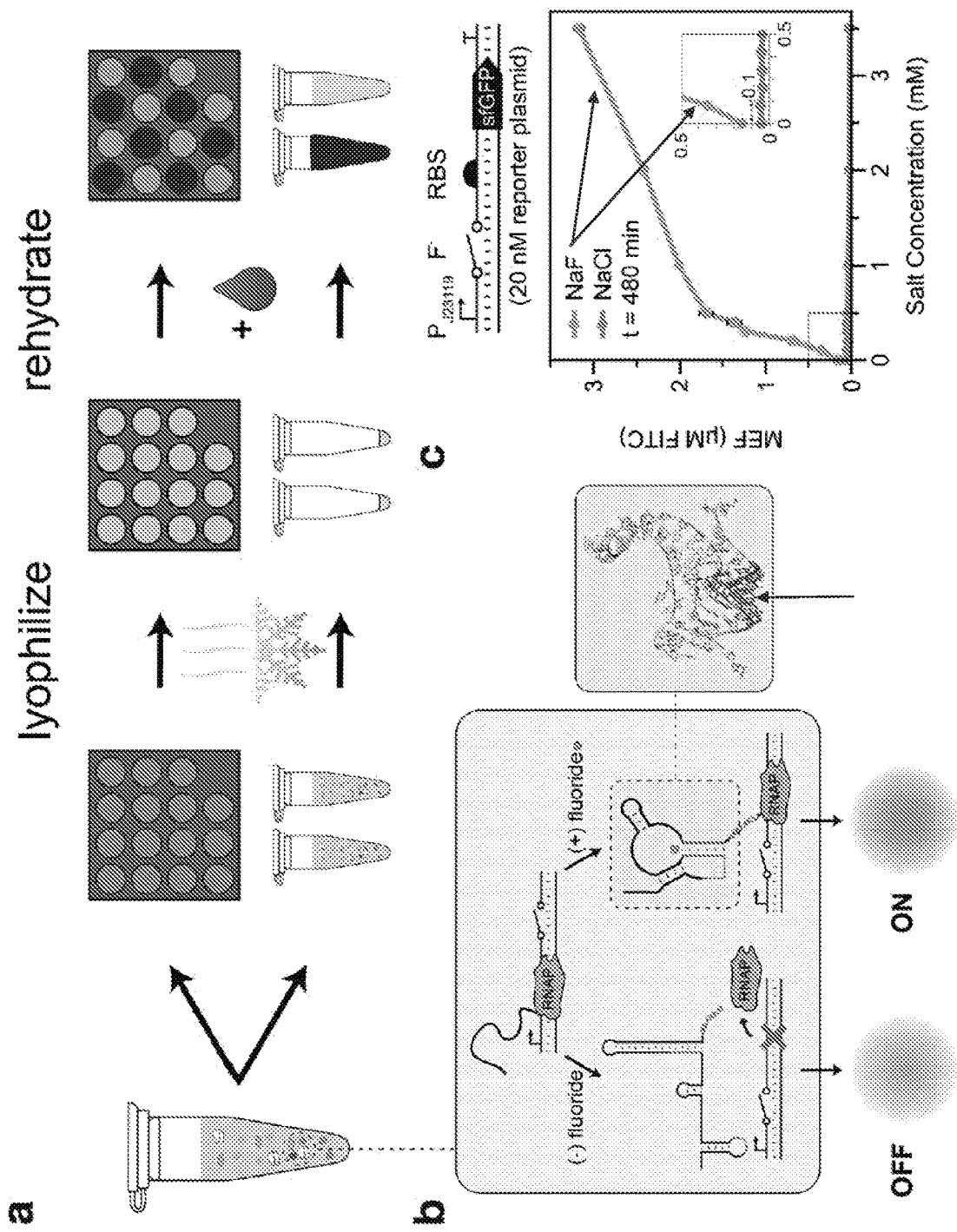
FIG. 1. Cell-free fluoride biosensor engineering strategy. (a) Schematic for lyophilization of a cell-free reaction in tubes or on paper disks. Rehydration with a water sample allows the designed biosensing reaction to proceed to yield a detectable signal. (b) Schematic for fluoride riboswitch-mediated transcriptional regulation in cell-free extract. The riboswitch folds cotranscriptionally into one of two mutually exclusive states, depending on the presence of fluoride. In the absence of fluoride, the riboswitch folds into a terminating hairpin, precluding downstream gene expression. Fluoride binding stabilizes a pseudoknot structure (red paired region (arrow), inset from PDB: 4ENC) that sequesters the terminator and enables the expression of downstream reporter genes. (c) Schematic of a cell-free fluoride biosensor, consisting of a DNA template encoding the fluoride riboswitch controlling the expression of sfGFP. Eight-hour endpoint fluorescence measurements for reactions containing NaF (top line) or NaCl (bottom line, along X axis) are shown below. Error bars represent one standard deviation from three technical replicates.

Our point-of-use diagnostic consists of a cell-free system containing a fluoride biosensor DNA template that can be lyophilized and stored. Rehydration activates the biosensor, which encodes the fluoride riboswitch and a reporter gene that produces a detectable output if fluoride is present (FIG. 1A, B). As a starting point, we sought to characterize the regulatory activity of the B. cereus crcB riboswitch in the cell-free reaction environment. Previous characterization of the riboswitch's cotranscriptional folding mechanism (FIG. 1B) confirmed that it functions with E. coli RNA polymerase[13], allowing us to use it in E. coli cell-free extract. We therefore constructed a reporter plasmid containing the riboswitch sequence followed by a strong ribosome binding site (RBS) and the coding sequence of the reporter protein superfolder green fluorescent protein (sfGFP), all placed downstream of a constitutive E. coli c° promoter (see FIG. 13 for plasmid details.).

After optimizing the level of Mg2+ within the reaction conditions for riboswitch performance (FIG. 5), we determined the fluoride sensor's dose-response to fluoride by titrating across a range of NaF concentrations. All tested conditions caused a measurable increase in expression over the OFF state, with activation seen at NaF concentrations as low as 0.1 mM (FIG. 1C, upper line and inset). This threshold is important, since 0.1 mM NaF is equivalent to the EPA's 2 ppm secondary maximum contaminant level for fluoride in drinking water, its most stringent risk threshold[14]. However, because the signal-to-noise ratio at 0.1 mM NaF is below 3, we estimated the reliable lower limit of detection to be 0.2 mM NaF. Importantly, the system also has low leak—we observed minimal activation of gene expression in the absence of NaF. Titration of identical concentrations of NaCl showed no increase in expression at any condition, demonstrating that the riboswitch is highly specific for fluoride (FIG. 1C, bottom line). This result corroborates a previous and more extensive characterization in E. coli of the switch's specificity for fluoride[12]. Thus, without any optimization of riboswitch structure or function, the sensor can discriminate health-relevant concentrations of fluoride dosed into laboratory water samples.

Figure 2:
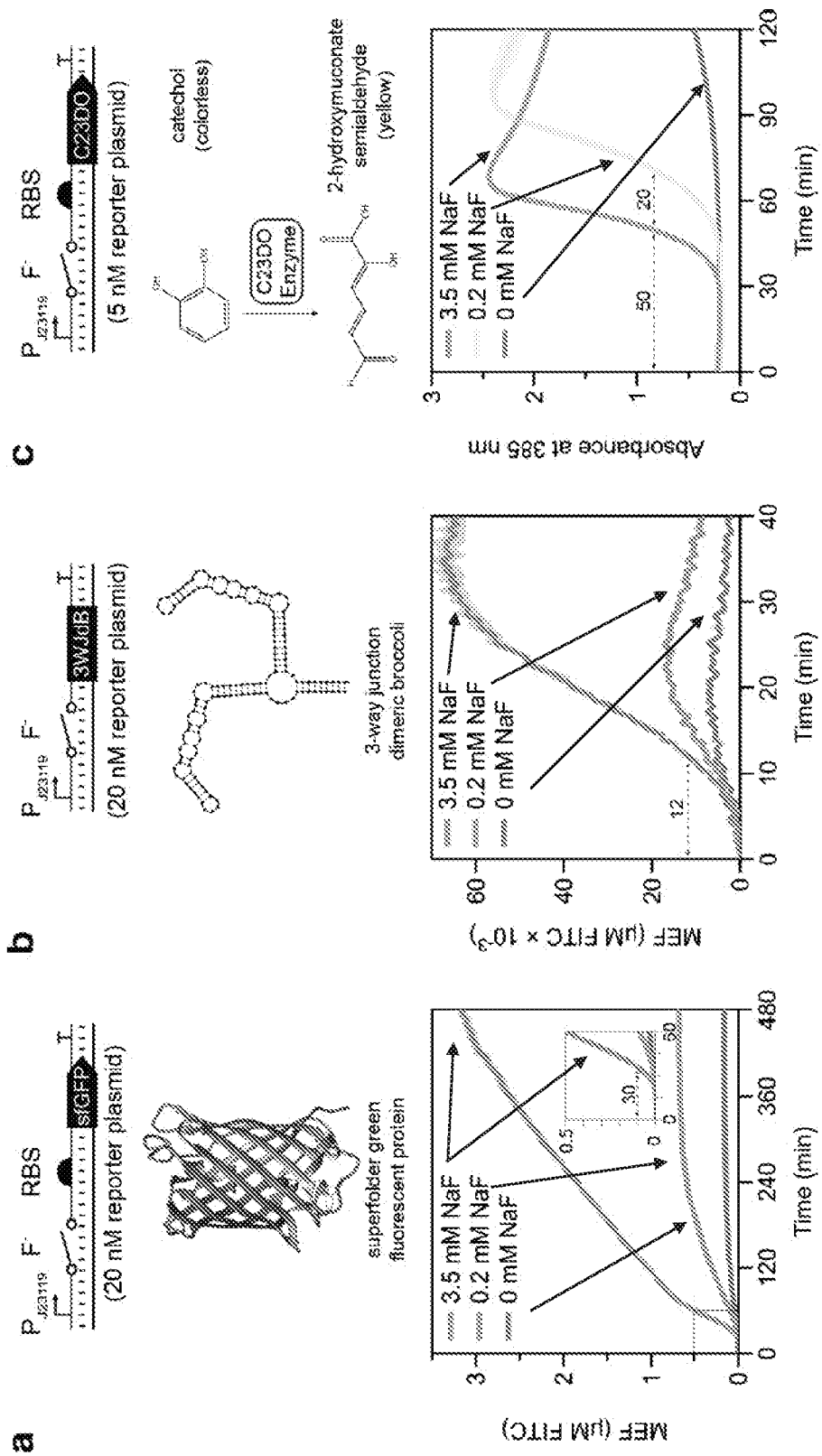
FIG. 2. Riboswitch modularity allows fluorescent protein, RNA aptamer and enzymatic colorimetric reporter outputs. Biosensor DNA template layouts and concentrations shown above reporter information and characterization data for that reporter. (a) Superfolder GFP (sfGFP) reporter (structure from PDB: 2B3P). Time course of fluorescence in the presence of 3.5 mM NaF (top line), 0.2 mM NaF (middle line), or 0 mM NaF (bottom line). (b) 3-way junction dimeric Broccoli reporter (structure predicted from NUPACK[15]). Time course of fluorescence in the presence of 3.5 mM NaF (top line), 0.2 mM NaF (middle line) and 0 mM NaF (bottom line). (c) Catechol (2,3)-dioxygenase (C23DO) reporter. Reaction scheme shows the cleavage of the colorless catechol molecule into the yellow 2-hydroxymuconate semialdehyde. Time course of absorbance at 385 nm in the presence of 3.5 mM NaF (darker upper line), 0.2 mM NaF (pale upper line), and 0 mM NaF (bottom line). For each plot, time course trajectories are marked by arrows and represent average and error shading represents one standard deviation from three technical replicates. (a) and (b) are reported in mean equivalent fluorescence (MEF).

B. Evaluation of Reporters to Decrease Reaction Time and Improve Detection Limits Biosensor field deployment requires an output that can be quickly read with minimal supplemental equipment[16]. Using the maximally activating fluoride concentration (3.5 mM), reactions achieved measurable signal above the no-fluoride OFF state in 30 minutes at 30° C., with overall 20-fold activation relative to the no-fluoride condition at the end of the 8-hour experiment (FIG. 2A). Despite this, the sensor's ON state was not distinguishable by eye for several hours even after excitation with a blue LED, presenting the need for a faster reporter.

We hypothesized that we could accelerate the sensor's response with a 3-way junction dimeric Broccoli (3WJdB)[17] reporter, an RNA aptamer that activates fluorescence of its DFHBI-1T ligand upon transcription, eliminating delays caused by translation. At all tested NaF concentrations, 3WJdB produced a signal detectable over background within 12 minutes at 30° C. (FIG. 2B), more than twice as fast as could be achieved with sfGFP (FIG. 2A). Interestingly, this result also confirms that the fluoride riboswitch is compatible with RNA reporters, despite the potential for misfolding with the upstream riboswitch sequence. However, despite the improvement in speed, exchanging sfGFP for 3WJdB resulted in a 50-fold reduction in the sensor's fluorescent output at the maximally activating tested condition. Thus, although the RNA-level output is preferable for its speed relative to the sfGFP output if a plate reader is accessible, it is not bright enough to use for field deployment.

As an alternative to a fluorescent output, we used the colorimetric enzyme catechol (2,3)-dioxygenase (C23DO) as a reporter. C23DO has previously been used in genetically-encoded biosensors for plant viruses[18] and produces a visible reporter output by oxidizing its colorless catechol substrate to the yellow-colored 2-hydroxymuconate semialdehyde[19]. This color change allows gene expression to be read out either by light absorbance at 385 nanometers on a plate reader or by the appearance of a yellow color, visible to the naked eye. All tested fluoride concentrations produced a visible output within 70 minutes at 30° C., which we empirically defined as an absorbance of 0.8 based on our previous observations (FIG. 2C)[18]. Notably, there was only a 20-minute time separation between the minimally and maximally activating conditions, highlighting the ability of enzymatic reporters to quickly amplify weak signals. Consistent with previous uses of C23DO as a reporter in a cell-free reaction[19], we observed a decay in the absorbance signal after it reached peak activation, possibly due to 2-hydroxymuconate semialdehyde degradation. This effect does not compromise sensor robustness because differences in activation for an enzymatic reporter are determined by differences in time to observable signal rather than final signal magnitude, which is determined by the amount of substrate supplied. One disadvantage of this strategy is that activation time does not linearly correlate with fluoride concentration, limiting the sensor to only supplying a binary presence/absence result within a specified time window[16]. Despite this, the sensor's sensitivity and low leak make this presence/absence result diagnostically informative, which combined with the advantages of an easily visualized output and reasonable time to detection made C23DO our reporter of choice for a field-deployable diagnostic.

C. Evaluation of Reaction Conditions to Improve Detection Limits

We next took steps to optimize our sensor to detect fluoride near the EPA's secondary maximum contaminant limit of 2 ppm (100 μM). We obtained a robust ON signal with our original design, but the sensor began to leak without fluoride after 90 minutes (FIG. 2C, bottom line), complicating detection for trace amounts of fluoride. We attempted to mitigate this problem by reducing the amount of reporter DNA supplied to the reaction from 5 nM to 3 nM to diminish the sensor's output. In doing so, we completely suppressed leak while detecting 100 μM NaF over background (FIG. 3A), but at the cost of significantly delaying activation. We could detect as low as 50 μM NaF over background in this leakless sensor, but only during an extended incubation that did not reach a visually detectable threshold within six hours.

Figure 3:
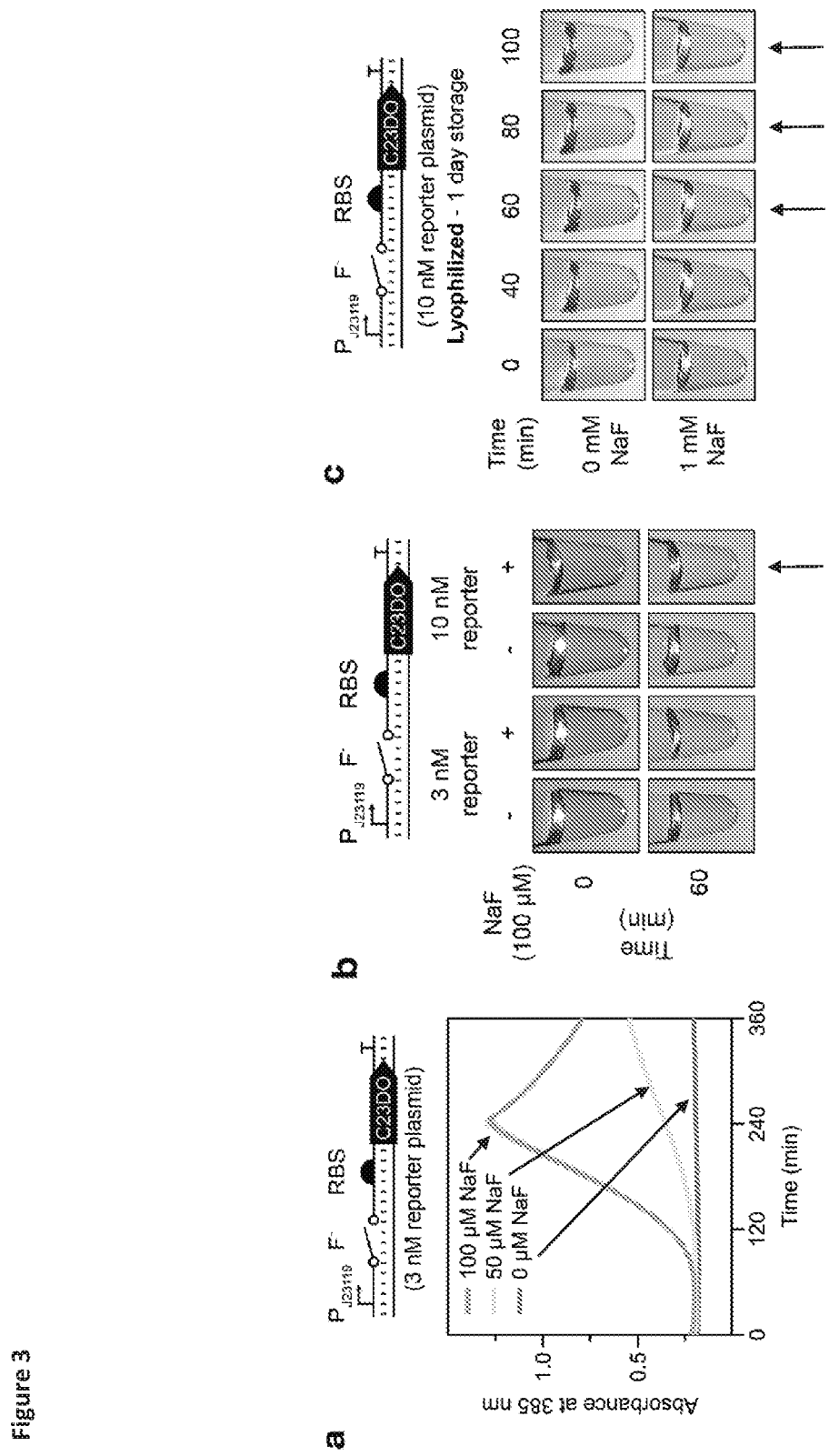
FIG. 3. Colorimetric reporters enable fluoride sensing at environmentally relevant concentrations. (a) Time course trajectories of 385 nm absorbance as measured by plate reader in the presence of 100 µM NaF (top line), 50 µM NaF (middle line), and 0 µM NaF (bottom line) using C23DO as a reporter and incubated at 30° C. Trajectories, each marked with an arrow, represent average and error shading represents one standard deviation from three technical replicates. (b) Color change observed after 1-hour for two different reporter template concentrations with and without 100 µM NaF. Tubes were mixed by pipetting and incubated at 37° C.

To solve this dilemma and maintain a practical incubation time, we sought a strategy whereby tests could be interpreted as "ON" only if the yellow color appeared within some externally specified time window. Under these constraints, sensor leak is not a problem as long as the difference in timescale between the ON and OFF state is suitably longer than the test time. To implement this strategy, we increased biosensor DNA concentration to 10 nM and also increased the temperature of the CFE reaction to 37° C. Under these conditions, activation by 100 μM NaF resulted in a clear color change in sixty minutes with no visible leak in the OFF condition (FIG. 3B, FIG. 6). The same conditions using 3 nM DNA template resulted in no color change within 60 minutes. This result highlights an appreciable advantage afforded by the open reaction environment of cell-free systems: the sensor's limit of detection can be tuned simply by manipulating the reaction time and the DNA concentration of the biosensor.

D. Lyophilization and Stability Testing

Recent work demonstrates that CFE reactions can be lyophilized and rehydrated when needed for on-demand biomanufacturing, nucleic acid detection, and educational activities[6,7,20,21]. To expand these applications to point-of-use small molecule detection, we next aimed to demonstrate that fluoride biosensor reactions maintain functionality after being lyophilized. We measured the impact of lyophilization on fluoride detection by lyophilizing reactions containing 10 nM C23DO reporter plasmid overnight. The reactions were then rehydrated with laboratory grade Milli-Q water (FIG. 3C, top) or water containing 1 mM NaF (FIG. 3C, bottom) and incubated at 37° C. Time-lapse photography shows visible activation within 60 minutes in the 1 mM NaF condition with no leak observed within 100 minutes in the no-fluoride condition. This finding, consistent with other recent reports from lyophilized cell-free systems[6,7,20,21] indicates that sensing by the fluoride riboswitch in CFE reactions is not disrupted by the lyophilization process.

We also tested the viability of lyophilized reactions stored over longer periods of time. After lyophilization, reaction tubes were wrapped in Parafilm and stored in Drierite for 3 months in darkness at room temperature and atmospheric pressure before being removed and rehydrated with laboratory grade Milli-Q water or water containing 1 mM NaF. The sample rehydrated with 1 mM NaF showed strong activation within one hour, with no leak observed in the no-fluoride condition (FIG. 7). Interestingly, lyophilization appeared to suppress leak in the no-fluoride condition without impacting the ability to activate expression with fluoride. The maintained viability of reactions after three months indicates that storage in desiccant and light shielding to prevent catechol oxidation are the only requirements for long-term storage of lyophilized cell-free reactions, a crucial step towards field-deployment.

E. Mock Field Testing

Components of environmental water samples, particularly natural ions like sodium, magnesium, or potassium, could poison cell-free reactions upon rehydration. These "matrix effects" would then impede the translation of a sensor from lab experiments to field testing and must be accounted for in a field-deployable diagnostic. To test the robustness of our system against matrix effects, we created mock fluoride-containing field samples by sampling water from a municipal tap, Lake Michigan, and an outdoor swimming pool, with Milli-Q water used as a control. NaF was then added to each sample to a final concentration of 1 mM. The biosensing reactions were prepared as before and pipetted into PCR tubes (FIG. 4A, top) or spotted on BSA-treated chromatography paper (FIG. 4A, bottom) before being lyophilized overnight. After lyophilization, reactions were immediately rehydrated with either unaltered mock field sample (-condition) or mock field sample containing 1 mM NaF (+condition) and incubated at 37° C. for one hour. For all fluoride-containing samples both in tubes and on paper, a color change was observed within one hour, with no color development in any of the no-fluoride conditions. These results confirm that the fluoride biosensor is robust against the unfiltered environmental samples tested and can be used in real-world conditions.

F. Field Testing

As the culmination of our optimization process, we tested our sensor's ability to accurately classify fluoride-containing samples in the field. We specifically sought to follow a previously published environmental fluoride study that used conventional methods to sample and test publicly available natural and municipal water sources near the Irazu volcano in Cartago, Costa Rica, an area shown to have elevated fluoride levels (FIG. 8)[23]. To do this, we manufactured lyophilized fluoride biosensor reactions and transported them to Costa Rica using our simplified desiccant packaging (FIG. 9) for field testing. Sampling regions identified in the previous study[23], we collected samples in 50 mL conical tubes and tested for fluoride in batch by adding unprocessed water to lyophilized reactions in PCR tubes via single-use exact volume transfer pipettes (FIG. 9B).

All field-testing was done onsite in Costa Rica without access to laboratory resources or equipment. Reactions were incubated at approximately 37° C. by being held in the armpit, with reaction time increased to 5 hours to control for delayed activation caused by the imprecision of body heat incubation and low environmental fluoride concentrations[18]. A strong yellow color developed in every positive control reaction within an hour, confirming robustness to reaction poisoning by potential sample matrix effects (FIG. 14). No activation was observed within 5 hours in any samples with fluoride concentrations less than 50 μM (~1 ppm) as measured in cross-validation with a commercial fluoride-sensing electrode. However, a visible color change was observed after 3.5 hours in a water sample collected from a roadside ditch measured to have a fluoride concentration of 60 μM (FIG. 4B). This delayed activation aligns with our previous characterization in detecting trace concentrations of fluoride below 100 μM (FIG. 3A). For all samples, the commercial electrode measurement confirmed the conclusions drawn from the cell-free sensors, with no false positives or false negatives observed under any conditions (n=9) (FIG. 14). By accurately detecting levels of fluoride relevant to public health concern thresholds in a real-world water source with minimal supplementary equipment, we have shown that lyophilized fluoride biosensor CFE reactions can be effectively used as low-cost, point-of-use diagnostics, demonstrating the potential of engineered biosensor elements for small molecule detection in the field.

G. Discussion

In this work, we have demonstrated that a fluoride riboswitch can be implemented in a CFE system to act as a field-deployable diagnostic for environmental water samples. To the best of our knowledge, this is the first demonstration of a cell-free riboswitch-based biosensor that can detect health-relevant small molecules at regulatory levels within the field. Importantly, this work represents a significant improvement in efficacy over commercially available consumer kits (FIG. 10) and provides significant simplification and cost savings over gold standard electrochemical methods of fluoride detection, which cost hundreds to thousands of dollars and are cumbersome to use even for scientifically skilled operators. In contrast, our biosensors can currently be made for $0.40/reaction20, only require a drop of water, and are robust to temperature variation, enabling incubation with body heat.

A key strength of cell-free biosensing is that biochemical parameters such as cofactor and DNA concentration can be easily tuned to reduce leak and improve dynamic range, which has been a historically difficult challenge for riboswitch engineering in cells. Furthermore, since riboswitches are cis-acting, only one DNA template concentration needs to be tuned per sensor, simplifying the optimization space relative to trans-acting RNA or protein regulators. When optimizing these reactions for the field, we found that reactions lyophilized in PCR tubes had advantages over paper-based reactions, which rapidly dried out even when incubated in sealed, humidified containers. This effect was exacerbated by the longer incubation times required for low analyte concentrations, variabilities in ambient temperature, and the practical difficulty of equipment-free incubation of paper sensors using body heat, making the tube format much more amenable to the challenges of field deployment.

This work also highlights the feasibility of using transcriptional riboswitch-mediated gene expression to convert weak-binding RNA aptamers into functional biosensors. We were surprised to find that the B. cereus crcB riboswitch activated so well in an E. coli cell-free lysate system, given the sophisticated nature of its folding mechanism and transcriptional readthrough observed both in vitro and in vivo[13,24] Transcriptional riboswitches often show weak activation due to the short timescales of their regulatory decision-making, resulting in sensitivities that are kinetically, rather than thermodynamically limited[25]. Coupling transcriptional riboswitches to enzymatic outputs like C23DO can amplify weak signals, since each reporter enzyme turns over multiple molecules of substrate[26]. The combined kinetic mechanism of switching and the signal amplification afforded by a colorimetric reporter resulted in our sensor achieving a limit of detection of 50 µM, less than half of the lowest previously measured KD for any fluoride aptamer[27]. Thus, this work is a powerful example of why considering only thermodynamic binding affinities during aptamer selection can exclude promising, diagnostically relevant sensors.

The strategies we present here could be applied to optimize the performance of a large number of natural riboswitches for the detection of metabolites and ions relevant to environmental and human health monitoring[28]. Additionally, the compatibility of CFE reactions for high-throughput screening[29] and the simple format of our DNA expression construct could be used to characterize the thousands of "orphan" riboswitches that have been bioinformatically identified but bind to unknown ligands[30]. We imagine that these strategies could even be used to re-engineer riboswitches to have novel function[31-33]. As the rules of riboswitch mechanisms are deciphered at deeper levels[13,34-36], we hope to reach a sufficient understanding to design their functional properties to meet the global needs for field-deployable environmental and health diagnostics.

Materials and Methods

Plasmid Construction. Plasmids were assembled using Gibson assembly (New England Biolabs, Cat #E2611S) and purified using a Qiagen QIAfilter Midiprep Kit (QIAGEN, Cat #12143). pJBL7025 and pJBL7026 were assembled from pJBL3752. A table of all plasmid sequences can be found in the tables presented in FIG. 12. All plasmids are being deposited in Addgene with accession numbers 128809-128811.

Extract Preparation. Extracts were prepared according to published protocols using sonication and postlysis processing in the Rosetta2 (DE3) pLysS strain[10]. Briefly, cells are plated on a chloramphenicol-selective agar plate and incubated overnight then used to inoculate a 20 mL overnight starter culture for a 1 L final culture. This culture is grown to an optical density (OD600) of 3.0±0.2 then pelleted and lysed by sonication before centrifugation for 10 minutes at 4° C. and 12,000 g. After lysis, extracts were incubated with shaking for 80 minutes at 37° C. and 200 rpm then recentrifuged under the same conditions. The supernatant was injected into a 10K MWCO dialysis cassette (ThermoFisher, 66380) and dialyzed at 4° C. for three hours before a final centrifugation under the same conditions and snap-freezing in liquid nitrogen.

CFE Experiment. CFE reactions were prepared according to established protocols[10]. Briefly, reactions are composed of cell extract, a reaction buffer containing NTPs, amino acids, buffering salts, crowding agents, and an energy source, and a mix of template DNA and inducers in an approximately 30/30/40 ratio. Between reactions, the only conditions varied are DNA template and concentration, inducer concentration, and buffering magnesium glutamate concentration, the last of which is optimized by extract. Optimal magnesium glutamate concentration was 20 mM for shelf stability and field deployment experiments and 12 mM for all other data. Little variability was seen in extract performance between batches using the appropriate optimal magnesium concentrations (FIG. 11).

For an example reaction setup, refer to the Supplemental Experimental Design Spreadsheet. All kinetic CFE reactions were prepared on ice in triplicate at the 10 µL scale. 33 µL of a mixture containing the desired reaction components was prepared and then 10 µL was pipetted into three wells of a 384-well plate (Corning, 3712), taking care to avoid bubbles. Plates were sealed (ThermoScientific, 232701) and kinetic data was monitored on a BioTek Synergy H1m plate reader for sfGFP (20 nM reporter plasmid, emission/excitation: 485/520 nm every five minutes for 8 hours at 30° C.), C23DO (variable reporter plasmid concentration, 385 nm absorbance every 30 seconds for 4-6 hours at 30° C.), and 3WJdB (20 nM reporter plasmid, emission/excitation 472/507 nm every 30 seconds for 2 hours at 30° C.). C23DO reactions were supplemented with 1 mM catechol and 3WJdB reactions were supplemented with 20 µM DFHBI-1 T. For all fluorescence experiments, a no-DNA negative control was prepared in triplicate for every extract being tested. All reported fluorescence values have been baselinesubtracted by the average of three samples from the no-DNA condition. Baseline subtraction was not performed for catechol reactions because reaction progress is determined from time to activation rather than maximal absorbance value. For the data depicted in FIG. 1C, NaF and NaCl titrations were performed in separate experiments.

Mean Equivalent Fluorescence Calibration. Fluorescence measurements were calibrated to a standard curve of fluorescein isothiocyanate (FITC) fluorescence to give standardized fluorescence units of μM equivalent FITC following a previously established procedure[37]. Briefly, serial dilutions were performed from a 50 μM stock and prepared in a pH 9.5, 100 mM sodium borate buffer. Fluorescence values for these samples were read at an excitation wavelength of 485 nm and emission wavelength of 515 nm for sfGFP and an excitation wavelength of 472 nm and emission wavelength of 507 nm for 3WJdB. These values were then used to calculate a linear conversion factor relating the plate reader's output in arbitrary units to the FITC standard curve.

Lyophilization. All lyophilization was performed in a Labconco FreeZone 2.5 Liter—84° C. Benchtop Freeze Dryer (Cat #710201000). A CFE reaction master mix was prepared and split into 20 μL aliquots in PCR strip tubes. Tube caps were then pierced with a pin and strips were wrapped in aluminum foil before being flash frozen in liquid nitrogen and lyophilized overnight at 0.04 mbar. After lyophilization, pierced PCR strip tube caps were replaced. Tubes were then sealed with parafilm and placed directly into Drierite (Cat #11001) for storage at room temperature (FIG. 9).

Paper Sensors. Individual sensors were punched out of Whatman 1 CHR chromatography paper (3001-861) using a Swingline Commercial Desktop Punch (A7074020). Tickets were then placed in a petri dish and immersed in 4% BSA for one hour before being transferred to a new dish and left to air dry overnight. After drying, tickets were spotted with 20 μL of CFE reaction and placed in plastic jars (QOSMEDIX 29258), which were loosely capped and wrapped in aluminum foil before being flash frozen in liquid nitrogen and lyophilized overnight at 0.04 mbar. For testing, tickets were transferred to new jars and rehydrated with 20 μL of sample solution. Jars were then closed and sealed with parafilm before incubation for one hour at 37° C.

Field Deployment. 20 μL lyophilized reactions were prepared with 10 nM pJBL7025 and 1 mM catechol. As a positive control, additional reactions were lyophilized after being pre-enriched with 1 mM NaF. The table presented in FIG. 14 contains a complete list of sample site locations and water sources tested. 50 mL water samples were collected and stored in Falcon tubes (Fisher Scientific, Cat #14-432-22) without any processing or filtration. Reactions were rehydrated by using 20 μL exact volume transfer pipettes (Thomas Scientific, 1207F80) to pull from collected samples. Three reactions were run at each sample site: (1) a positive control rehydrated with the sample, (2) a blank reaction rehydrated with the sample, and (3) a negative control reaction rehydrated with purified water to test for any reaction leak. Reactions were placed in a plastic bag and incubated at body temperature in the armpit for five hours using established protocols and marked as activated if a visible yellow color was observed[18]. Quantitative measurements of fluoride concentration of the same sample were taken with an Extech ExStik Waterproof Fluoride Meter (Cat #FL700).

Image Capture. All images were captured with via cell phone camera, with no specialized photography setup and no post-capture editing done aside from cropping image borders. Tubes were illuminated from below via desk lamp to highlight reaction color change. Paper sensors were illuminated from above via desk lamp and photographed without removal from the plastic jars used for incubation.

REFERENCES (1) World Health Organization. World Health Statistics 2016: Monitoring Health for the SDGs Sustainable Development Goals; World Health Organization, 2016.
(2) Onda, K.; LoBuglio, J.; Bartram, J. Global Access to Safe Water: Accounting for Water Quality and the Resulting Impact on MDG Progress. Int. J. Environ. Res. Public Health 2012, 9 (3), 880-894.
(3) Maheshwari, R. C. Fluoride in Drinking Water and Its Removal. J. Hazard. Mater. 2006, 137 (1), 456-463.
(4) World Health Organization. Guidelines for Drinking-Water Quality. WHO Chron. 2011, 38 (4), 104-108.
(5) Zhou, Y.; Zhang, J. F.; Yoon, J. Fluorescence and Colorimetric Chemosensors for Fluoride-Ion Detection. Chem. Rev. 2014, 114 (10), 5511-5571.
(6) Pardee, K.; Green, A. A.; Ferrante, T.; Cameron, D. E.; DaleyKeyser, A.; Yin, P.; Collins, J. J. Paper-Based Synthetic Gene Networks. Cell 2014, 159 (4), 940-954.
(7) Pardee, K.; Green, A. A.; Takahashi, M. K.; Braff, D.; Lambert, G.; Lee, J. W.; Ferrante, T.; Ma, D.; Donghia, N.; Fan, M. Rapid, Low-Cost Detection of Zika Virus Using Programmable Biomolecular Components. Cell 2016, 165 (5), 1255-1266.
(8) Grawe, A.; Dreyer, A.; Vornholt, T.; Barteczko, U.; Buchholz, L.; Drews, G.; Ho, U. L.; Jackowski, M. E.; Kracht, M.; Luders, J. A Paper-Based, Cell-Free Biosensor System for the Detection of Heavy Metals and Date Rape Drugs. PLoS One 2019, 14 (3), e0210940.
(9) Gupta, S.; Sarkar, S.; Katranidis, A.; Bhattacharya, J. Development of a Cell-Free Optical Biosensor for Detection of a Broad Range of Mercury Contaminants in Water: A Plasmid DNA-Based Approach. ACS Omega 2019, 4 (5), 9480-9487.
(10) Silverman, A.; Kelley-Loughnane, N.; Lucks, J. B.; Jewett, M. C. Deconstructing Cell-Free Extract Preparation for in Vitro Activation of Transcriptional Genetic Circuitry. ACS Synth. Biol. 2018, 8 (2), 403-414.
(11) Carlson, E. D.; Gan, R.; Hodgman, C. E.; Jewett, M. C. Cell-Free Protein Synthesis: Applications Come of Age. Biotechnol. Adv. 2012, 30 (5), 1185-1194.
(12) Baker, J. L.; Sudarsan, N.; Weinberg, Z.; Roth, A.; Stockbridge, R. B.; Breaker, R. R. Widespread Genetic Switches and Toxicity Resistance Proteins for Fluoride. Science (80-.). 2012, 335 (6065), 233-235.
(13) Watters, K. E.; Strobel, E. J.; Angela, M. Y.; Lis, J. T.; Lucks, J. B. Cotranscriptional Folding of a Riboswitch at Nucleotide Resolution. Nat. Struct. Mol. Biol. 2016, 23 (12), 1124.
(14) Doull, J.; Boekelheide, K.; Farishian, B. G.; Isaacson, R. L.; Klotz, J. B.; Kumar, J. V; Limeback, H.; Poole, C.; Puzas, J. E.; Reed, N. M. R. Fluoride in Drinking Water: A Scientific Review of EPA's Standards. Natl. Acad. Washingt. 2006, 205-223.
(15) Zadeh, J. N.; Steenberg, C. D.; Bois, J. S.; Wolfe, B. R.; Pierce, M. B.; Khan, A. R.; Dirks, R. M.; Pierce, N. A. NUPACK: Analysis and Design of Nucleic Acid Systems. J. Comput. Chem. 2011, 32 (1), 170-173.
(16) McNerney, M. P.; Zhang, Y.; Steppe, P.; Silverman, A. D.; Jewett, M. C.; Styczynski, M. P. Point-of-Care Biomarker Quantification Enabled by Sample-Specific Calibration. Sci. Adv. 2019, 5 (9), eaax4473.

(17) Alam, K. K.; Tawiah, K. D.; Lichte, M. F.; Porciani, D.; Burke, D. H. A Fluorescent Split Aptamer for Visualizing RNA-RNA Assembly In Vivo. ACS Synth. Biol. 2017, 6 (9), 1710-1721.
(18) Verosloff, M.; Chappell, J.; Perry, K. L.; Thompson, J. R.; Lucks, J. B. PLANT-Dx: A Molecular Diagnostic for Point-of-Use Detection of Plant Pathogens. ACS Synth. Biol. 2019, 8 (4), 902-905.
(19) Chappell, J.; Westbrook, A.; Verosloff, M.; Lucks, J. B. Computational Design of Small Transcription Activating RNAs for Versatile and Dynamic Gene Regulation. Nat. Commun. 2017, 8 (1), 1051.
(20) Stark, J. C.; Huang, A.; Nguyen, P. Q.; Dubner, R. S.; Hsu, K. J.; Ferrante, T. C.; Anderson, M.; Kanapskyte, A.; Mucha, Q.; Packett, J. S.; et al. BioBits™ Bright: A Fluorescent Synthetic Biology Education Kit. Sci. Adv. 2018, 4 (8), eaat5107.
(21) Huang, A.; Nguyen, P. Q.; Stark, J. C.; Takahashi, M. K.; Donghia, N.; Ferrante, T.; Dy, A. J.; Hsu, K. J.; Dubner, R. S.; Pardee, K.; et al. BioBits™ Explorer: A Modular Synthetic Biology Education Kit. Sci. Adv. 2018, 4 (8), eaat5105.
(22) Haklay, M.; Weber, P. Openstreetmap: User-Generated Street Maps. Ieee Pervas Comput 2008, 7 (4), 12-18.
(23) Rojas Zuniga, F.; Floor, G.; Malavassi, E.; Martinez Cruz, M.; Van Bergen, M. Fluorosis Dental En La Poblaciòn Infantil En Las Cercanias Del Volcàn Irazù, Costa Rica. Congr. Latinoam. Estud. Quìmica Paraguay 2014.
(24) Zhao, B.; Guffy, S. L.; Williams, B.; Zhang, Q. An Excited State Underlies Gene Regulation of a Transcriptional Riboswitch. Nat. Chem. Biol. 2017, 13 (9), 968-974.
(25) Wickiser, J. K.; Winkler, W. C.; Breaker, R. R.; Crothers, D. M. The Speed of RNA Transcription and Metabolite Binding Kinetics Operate an FMN Riboswitch. Mol. Cell 2005, 18 (1), 49-60.
(26) Karzbrun, E.; Shin, J.; Bar-Ziv, R. H.; Noireaux, V. Coarse-Grained Dynamics of Protein Synthesis in a Cell-Free System. Phys. Rev. Lett. 2011, 106 (4), 48104.
(27) Ren, A.; Rajashankar, K. R.; Patel, D. J. Fluoride Ion Encapsulation by Mg 2+ Ions and Phosphates in a Fluoride Riboswitch. Nature 2012, 486 (7401), 85.
(28) McCown, P. J.; Corbino, K. A.; Stav, S.; Sherlock, M. E.; Breaker, R. R. Riboswitch Diversity and Distribution. RNA 2017, 23 (7), 995-1011.
(29) Moore, S. J.; MacDonald, J. T.; Wienecke, S.; Ishwarbhai, A.; Tsipa, A.; Aw, R.; Kylilis, N.; Bell, D. J.; McClymont, D. W.; Jensen, K.; et al. Rapid Acquisition and Model-Based Analysis of Cell-Free Transcription-Translation Reactions from Nonmodel Bacteria. Proc. Natl. Acad. Sci. 2018, 115 (19).
(30) Greenlee, E. B.; Stav, S.; Atilho, R. M.; Brewer, K. I.; Harris, K. A.; Malkowski, S. N.; Mirihana Arachchilage, G.; Perkins, K. R.; Sherlock, M. E.; Breaker, R. R. Challenges of Ligand Identification for the Second Wave of Orphan Riboswitch Candidates. RNA Biol. 2018, 15 (3), 377-390.
(31) Boussebayle, A.; Torka, D.; Ollivaud, S.; Braun, J.; Bofill-Bosch, C.; Dombrowski, M.; Groher, F.; Hamacher, K.; Suess, B. Next-Level Riboswitch Development Implementation of Capture-SELEX Facilitates Identification of a New Synthetic Riboswitch. Nucleic Acids Res. 2019, 47 (9), 4883-4895.
(32) Espah Borujeni, A.; Mishler, D. M.; Wang, J.; Huso, W.; Salis, H. M. Automated Physics-Based Design of Synthetic Riboswitches from Diverse RNA Aptamers. Nucleic Acids Res. 2015, 44 (1), 1-13.
(33) Wu, M. J.; Andreasson, J. O. L.; Kladwang, W.; Greenleaf, W. J.; Das, R. Automated Design of Diverse Stand-Alone Riboswitches. ACS Synth. Biol. 2019, 8 (8), 1838-1846.
(34) Frieda, K. L.; Block, S. M. Direct Observation of Cotranscriptional Folding in an Adenine Riboswitch. Science (80-.). 2012, 338 (6105), 397-400.
(35) Drogalis, L. K.; Batey, R. T. Requirements for Efficient Cotranscriptional Regulatory Switching in Designed Variants of the *Bacillus Subtilis* PbuE Adenine-Responsive Riboswitch. bioRxiv 2018. https://doi.org/10.1101/372573.
(36) Strobel, E. J.; Cheng, L.; Berman, K. E.; Carlson, P. D.; Lucks, J. B. A Ligand-Gated Strand Displacement Mechanism for ZTP Riboswitch Transcription Control. Nat. Chem. Biol. 2019, 15 (11), 1067-1076.
(37) Alam, K. K.; Jung, J. K.; Verosloff, M. S.; Clauer, P. R.; Lee, J. W.; Capdevila, D. A.; Pasten, P. A.; Giedroc, D. P.; Collins, J. J.; Lucks, J. B. Rapid, Low-Cost Detection of Water Contaminants Using Regulated In Vitro Transcription. bioRxiv 2019. https://doi.org/10.1101/619296.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of detecting fluoride in a liquid sample, comprising:
   (i) obtaining a sample which may or may not contain fluoride;
   (ii) adding the sample to a cell-free protein synthesis (CFPS) reaction comprising a fluoride-sensing riboswitch, wherein if fluoride is present in the sample at a concentration of about 0.05 mM or higher, then a detectable output is generated within less than about 300 minutes.

2. The method of claim 1, wherein the sample comprises an environmental sample, an industrial sample, or a biological sample.

3. The method of claim 2, wherein the sample comprises the environmental sample or the industrial sample, and wherein the environmental sample or the industrial sample further comprises water.

4. The method of claim 1, wherein the detectable output is generated within less than about 300, 240, 180, 120, 90, 60, 40, 30, 20, or 10 minutes.

5. The method of claim 1, wherein the CFPS reaction comprises:
   (a) a cell extract from a host strain that provides and/or regenerates one or more of: (i) energy; (ii) cofactors; (iii) enzymes used for cell-free sensing of the target molecule; or (iv) any combination thereof, and
   (b) exogenous supplied cell-free protein synthesis reagents not present in the cell extract that comprise at least one expression cassette.

6. The method of claim 5, wherein the expression cassette comprises: (i) a promoter; (ii) the fluoride-sensing riboswitch; (iii) a transcription terminator; and (iv) an encoded reporter.

7. The method of claim 6, wherein: (i) the promoter is selected from (a) a synthetic constitutive *E. coli* Promoter BBa_J23119_Spe1, and (b) a T7 promoter; (ii) fluoride-sensing riboswitch comprises the *Bacillus cereus* fluoride riboswitch sequence; (iii) the transcription terminator comprises the T1/TE double transcriptional terminator; and (iv) the encoded reporter is:
   (a) selected from a coding sequence for catechol 2,3-dioxygenase or a coding sequence for a fluorescent protein selected from GFP or a derivative thereof, and wherein the expression cassette further comprises a ribosome binding sequence: or
   (b) an RNA aptamer.

8. The method of claim 1, wherein the detectable output is a visual, electronic, or optical output generated by a reporter that is expressed in the CFPS reaction in the presence of fluoride.

9. The method of claim 7, wherein the detectable output is a visual, electronic, or optical output generated from an enzymatic reaction catalyzed by a reporter protein that is expressed from the encoded reporter, wherein the reporter protein is catechol 2,3-dioxygenase and the CFPS further comprises a colorimetric substrate for catechol 2,3-dioxygenase.

10. The method of claim 7, wherein the encoded reporter is a fluorogenic or colorimetric RNA aptamer.

11. The method of claim 10, wherein the fluorogenic aptamer is a 3-Way Junction Dimeric Broccoli aptamer and the CFPS further comprises a colorimetric substrate for the aptamer.

12. The method of claim 1, wherein the detectable output is luminescence, fluorescence, or visible color.

13. A device or kit comprising components for detecting fluoride in a liquid sample, wherein the components comprise preserved CFPS reaction components comprising a fluoride-sensing riboswitch, wherein the preserved CFPS reaction components are configured to generate a detectable output within less than about 300 minutes if fluoride is present in the sample at a concentration of about 0.05 mM or higher, and optionally wherein the preserved CFPS reaction components are preserved by freeze-drying.

14. The device or kit of claim 13, wherein the preserved CFPS reaction components are supported on a substrate which optionally is a paper substrate.

15. The device or kit of claim 14, wherein the paper substrate comprises components that are preserved by freeze-drying.

16. The device or kit of claim 13, further comprising a component for reading the detectable output, wherein the detectable output is a visual, electronic, or optical output generated by a reporter that is expressed in the preserved CFPS reaction in the presence of fluoride.

17. A platform for detecting fluoride in an environmental or biological sample, the platform comprising: components for performing a cell-free protein synthesis (CFPS) reaction comprising an expression cassette comprising (i) a promoter selected from (a) a synthetic constitutive *E. coli* PromoterBBa J23119 Spe1, and (b) a T7 promoter; (ii) a fluoride-sensing riboswitch comprising a *Bacillus cereus* fluoride riboswitch sequence; (iii) a transcription terminator comprising the T1/TE double transcriptional terminator; and (iv) an encoded reporter, wherein the encoded reporter is:
(a) selected from a coding sequence for catechol 2,3-dioxygenase or a coding sequence for a fluorescent protein selected from GFP or a derivative thereof, and wherein the expression cassette further comprises a ribosome binding sequence; or
(b) an RNA aptamer,
wherein the components for performing a cell-free protein synthesis (CFPS) reaction are configured to generate a detectable output within less than about 300 minutes if fluoride is present in the sample at a concentration of about 0.05 mM or higher.

* * * * *